United States Patent
Dorfman et al.

(10) Patent No.: US 11,207,679 B2
(45) Date of Patent: Dec. 28, 2021

(54) DNA EXTRACTION DEVICE

(71) Applicant: Regents of the University of Minnesota, Minneapolis, MN (US)

(72) Inventors: Kevin David Dorfman, Edina, MN (US); Paridhi Agrawal, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 97 days.

(21) Appl. No.: 16/383,129

(22) Filed: Apr. 12, 2019

(65) Prior Publication Data

US 2019/0314814 A1 Oct. 17, 2019

Related U.S. Application Data

(60) Provisional application No. 62/657,395, filed on Apr. 13, 2018.

(51) Int. Cl.
*B01L 3/00* (2006.01)
*C12N 15/10* (2006.01)

(52) U.S. Cl.
CPC .... *B01L 3/502715* (2013.01); *C12N 15/1003* (2013.01); *B01L 2300/0645* (2013.01); *B01L 2300/0861* (2013.01)

(58) Field of Classification Search
CPC ....... B01L 3/502715; B01L 2300/0861; B01L 2300/0645; B01L 2200/0631;
(Continued)

(56) References Cited

U.S. PATENT DOCUMENTS 6,827,830 B1 12/2004 Slater et al.
7,081,190 B2 * 7/2006 Dubrow ........... G01N 27/44747
204/454
(Continued)

FOREIGN PATENT DOCUMENTS

CN 102245305 11/2011
CN 206244806 U 6/2017
(Continued)

OTHER PUBLICATIONS

Brahmasandra et al. (SN Brahmasandra, VM Ugaz, DT Burke, CH Mastrangelo, MA Burns, Electrophoresis in Microfabricated devices using photopolymerized polyacrylamide gels and electrode-defined sample injection, Electrophoresis 22 (2001) 300-311) (Year: 2001).*
(Continued)

*Primary Examiner* — Joshua L Allen
(74) *Attorney, Agent, or Firm* — Shumaker & Sieffert, P.A.

(57) ABSTRACT

A DNA extraction device may include a substrate, at least one first side channel electrode, at least one second side channel electrode, optionally, at least one elongate central channel electrode, and a voltage source connected between the electrodes. The substrate defines an elongate central channel defining a major axis. A width of the elongate central channel is greater than its depth, and its depth is less than about 15 times a diameter of a cell to be introduced in the elongate central channel. The substrate also defines first and second side channels adjacent to the elongate central channel on opposite sides of the major axis. The substrate further defines first and second trapezoidally shaped connecting channels connecting the elongate central channel and the first and second side channels, respectively. The smaller parallel sides of the first and second trapezoidally
(Continued)

shaped connecting channels open to the respective side channels.

21 Claims, 13 Drawing Sheets

(58) Field of Classification Search
CPC ....... B01L 2400/0421; B01L 3/502761; C12N 15/1003; C12N 15/101
See application file for complete search history.

(56) References Cited

U.S. PATENT DOCUMENTS

| | | | |
|---|---|---|---|
| 9,101,933 B2 | 8/2015 | Hawell | |
| 2011/0174623 A1* | 7/2011 | Harrold | B01L 3/502753 204/547 |
| 2014/0057311 A1* | 2/2014 | Kamm | C12M 25/14 435/29 |
| 2017/0219523 A1* | 8/2017 | Shallan | B01D 71/50 |
| 2017/0252743 A1* | 9/2017 | Tegenfeldt | B01L 3/502761 |

FOREIGN PATENT DOCUMENTS

| | | | | |
|---|---|---|---|---|
| TW | 200523359 A | 7/2005 | | |
| TW | I252868 B | 4/2006 | | |
| WO | WO-2017087908 A1 * | 5/2017 | ....... | G01N 33/48721 |

OTHER PUBLICATIONS

Huang et al. (CP Huang, J Lu, H Seon, AP Lee, LA Flanagan, HY Kim, AJ Putnam, NL Jeon, Engineering microscale cellular niches for three-dimensional multicellular co-cultures, Lab Chip 9 (2009) 1740-1748), (Year: 2009).*
Pavesi et al. (A Pavesi, G Adriani, A Tay, ME Warkiani, WH Yeap, SC Wong, RD Kamm, Engineering a 3D microfluidic culture platform for tumor-treating field applications, Sci. Rep. 6 (2016) 26584) (Year: 2016).*
Farahat et al. (WA Farahat, LB Wood, IK Zervantonakis, A Schor, S Ong, D Neal, RD Kamm, HH Asada, Ensemble analysis of angiogenic growth in three-dimensional microfluidic cell cultures, PlosOne 7(5) (2012) e37333) (Year: 2012).*
Lin et al., "Addressable Electric Fields for Size-Fractioned Sample Extraction in Microfluidic Devices," Analytical Chemistry, vol. 77, No. 14, Jul. 15, 2005, 10 pp.
"DNA extraction," Wikipedia, retrieved from https://en.wikipedia.org/wiki/DNA_extraction, accessed on Jan. 8, 2020, 5 pp.
"Genomic DNA Isolation Kit (Cat. 24700, 24750, 24770)," Norgen Biotek, retrieved from https://norgenbiotek.com/product/genomic-dna-isolation-kit, accessed on Mar. 13, 2020, 1 pp.
"MagMax-96 DNA Multi-Sample Kit," Thermo Fisher, retrieved from https://www.thermofisher.com/order/catalog/product/4413021#/4413021, accessed on Mar. 13, 2020, 4 pp.
"MagneSil Genomic, Large Volume System," Promega, retrieved from https://www.promega.com/Products/Nucleic-Acid-Extraction/Genomic-DNA/MagneSil-Genomic-Large-Volume-System?catNum=A4082, accessed on Mar. 13, 2020, 5 pp.
"QIAGEN Genomic-tip 500/G," Qiagen, retrieved from https://www.qiagen.com/US/products/discovery-and-translational-research/dna-rna-purification/dna-purification/genomic-dna/qiagen-genomic-tip-500g/#orderinginformation, accessed on Mar. 13, 2020, 3 pp.
"DNA Extraction | Genomic Vision," Genomic Vision, retrieved from http://www.genomicvision.com/products/molecular-combing-platform/dna-extraction/, accessed on Mar. 13, 2020, 3 pp.
"MasterPure Complete DNA and RNA Purification Kit," Lucigen, retrieved from https://www.lucigen.com/MasterPure-Complete-DNA-and-RNA-Purification-Kit/, accessed on Mar. 13, 2020, 2 pp.
Ebeling et al., "Proteinase K from Tritirachium album Limber," European Journal of Biochemistry, vol. 47, May 15, 1974, 7 pp.
Farahat et al., "Ensemble Analysis of Angiogenic Growth in Three-Dimensional Microfluidic Cell Cultures," Pios One, vol. 7, Issue 5, May 25, 2012, 14 pp.
The UniProt Consortium, "UniProt: the universal protein knowledgebase," Nucleic Acids Research, vol. 45, Database Issue, Nov. 28, 2016, 12 pp.
Collins et al., "A New Initiative on Precision Medicine," The New England Journal of Medicine, vol. 372, Issue 9, Feb. 26, 2015, 3 pp.
Alkan et al., "Limitations of next-generation genome sequence assembly," Natural Methods, vol. 8, Issue 1, Jan. 2011, 9 pp.
Eid et al., "Real-Time DNA Sequencing from Single Polymerase Molecules," Science Magazine, vol. 323, Jan. 2, 2009, 8 pp.
Lam et al., "Genome mapping on nanochannel arrays for structural variation analysis and sequence assembly," Nature Biotechnology, vol. 30, No. 8, Aug. 2012, 18 pp.
Zheng et al., "Haplotyping germline and cancer genomes using high-throughput linked-read sequencing," Nature Biotechnology, vol. 34, No. 3, Mar. 2016, 28 pp.
Pendleton et al., Assembly and diploid architecture of an individual human genome via single-molecule technologies, Natural Methods, vol. 12, Issue 8, Aug. 2015, 24 pp.
Cao et al., "Rapid detection of structural variation in a human genome using nanochannel-base genome mapping technology," GigaScience, vol. 3, Issue 34, Dec. 30, 2014, 11 pp.
Jain et al., "Nanopore sequencing and assembly of a human genome with ultra-long reads," Nature Biotechnology, vol. 36, No. 4, Apr. 2018, 16 pp.
Stancu et al., "Mapping and phasing of structural variation in patient genomes using nanpore sequencing," Nature Communications, vol. 8, Nov. 6, 2017, 13 pp.
Schneider et al., "Evaluation of GRCh38 and de novo haploid genome assemblies demonstrates the enduring quality of the reference assembly," Genome Research, vol. 27, No. 5, May 2017, 16 pp.
Jain et al., "Linear assembly of a human centromere on the Y chromosome," Nature Biotechnology, vol. 36, No. 4, Apr. 2018, 10 pp.
Stankova et al., "BioNano genome mapping of individual chromosomes supports physical mapping and sequence assembly in complex plant genomes," Plant Biotechnology Journal, vol. 14, Nov. 13, 2015, 9 pp.
Zaremba-Niedzwiedzka, Asgard archaea illuminate the origin of eukaryotic cellular complexity, Nature, vol. 541, Jan. 19, 2017, 30 pp.
Kovacic et al., "Protection of megabase DNA from shearing," Oxford University Press, Nucleic Acids Research, vol. 23, No. 19, Aug. 29, 1995, 2 pp.
Kim et al., "A Microfluidic Technique for Quantification of Steroids in Core Needle Biopsies," American Chemical Society, Analytical Chemistry, vol. 87, Apr. 20, 2015, 8 pp.
Zimny et al., "Hydrogel droplet single-cell processing: DNA purification, handling, release, and on-chip linearization," Biomicrofluidics, vol. 12, Mar. 14, 2018, 9 pp.
Fangman, "Separation of very large DNA molecules by gel electrophoresis," Nucleic Acids Research, vol. 5, No. 3, Mar. 1978, 13 pp.
Kim et al., "Microfluidic sample preparation: cell lysis and nucleic acid purification," The Royal Society of Chemistry, Integrative Biology, vol. 1, Aug. 10, 2009, 13 pp.
Huang et al., "Engineering microscale cellular niches for three-dimensional multicellular co-cultures," Lab Chip, vol. 9, No. 12, Jun. 21, 2009, 16 pp.
Batchelor, "An Introduction to Fluid Dynamics," Cambridge University Press, (Applicant points out, in accordance with MPEP 609.04(a), that the year of publication, 2000, is sufficiently earlier than the effective U.S. filing date, so that the particular month of publication is not in issue.), 631 pp.
Gabrieli et al., "Selective nanopore sequencing of human BRCA1 by Cas9-assisted targeting of chromosome segments (CATCH)," Nucleic Acids Research, vol. 46, No. 14, May 18, 2018, 8 pp.
Akerman et al., "Single-and double-strand photocleavage of DNA by YO, YOYO, and TOTO," Oxford University Press, Nucleic Acids Research, vol. 24, No. 6, Jan. 29, 1996, 11 pp.

(56) References Cited

OTHER PUBLICATIONS

Narayanan et al., "Determination of agarose gel pore size: Absorbance measurements vis a vis other techniques," Institute of Physics Publishing, Journal of Physics: Conference Series, vol. 28, International Conference on Materials for Advanced Technologies, Symposium Y, Jul. 3-8, 2005, 5 pp.
Stone et al., "Engineering Flows in Small Devices: Microfluidics Toward a Lab-on-a-Chip," Annual Review of Fluid Mechanics, vol. 36, Jan. 9, 2004, 37 pp.
Gurrieri et al., "Trapping of megabase-sized DNA molecules during agarose gel electrophoresis," Proceedings of the National Academy of Sciences, vol. 96, Jan. 1999, 6 pp.
Brown et al., "Current techniques for sing-cell lysis," Journal of the Royal Society Interface, vol. 5, Apr. 15, 2008, 8 pp.
Kozlowski, "Proteome-pl: proteome isoelectric point database," Nucleic Acids Research, vol. 45, Oct. 13, 2016, 5 pp.
Seo et al., "De novo assembly and phasing of a Korean human genome," Nature, vol. 538, Oct. 13, 2016, 18 pp.
Marie et al., "Concentrating and labeling genomic DNA in a nanofluidic array," Royal Society of Chemistry, Nanoscale, vol. 10, Nov. 4, 2017, 7 pp.
Teague et al., "High-resolution human genome structure by single-molecule analysis," Proceedings of the National Academy of Science, vol. 107, No. 24, Jun. 15, 2010, 6 pp.
Fonslow et al., Fast Electrophoretic Separation Optimization Using Gradient Micro Free-Flow Electrophoresis, Analytical Chemistry, vol. 80, No. 9, May 1, 2008, 17 pp.
Pavesi et al., "Engineering a 3D microfluidic culture platform for tumor-treating field application," Scientific Reports, vol. 6, May 24, 2016, 10 pp.
Ugaz et al., "A versatile microfabricated platform for electrophoresis of double-and single-stranded DNA," Electrophoresis, vol. 24, Issue 1-2, Jan. 10, 2003, 7 pp.
Preibisch et al., "Globally optimal stitching of tiled 3D microscopic image acquisitions," Bioinformatics, vol. 24, No. 11, Apr. 3, 2009, 3 pp.
Huang et al., "Generation of Large-area Tunable Uniform Electric Fields in Microfluidic Arrays for Rapid DNA Separation," Electronic Devices Society of IEEE, International Electron Devices Meeting, Dec. 2001, 5 pp.
Persat et al., "Purification of Nucleic Acids from Whole Blood Using Isotachophoresis," Analytical Chemistry, vol. 81, No. 22, Nov. 15, 2009, 5 pp.
Culbertson et al., "Diffusion coefficient measurements in microfluidic devices," Talanta, vol. 56, Sep. 18, 2001, 9 pp.
Aronson et al., "Building the foundation for genomics in precision medicine," Nature, vol. 526, Oct. 15, 2015, 7 pp.
Mardis, "The impact of next-generation sequencing technology on genetics," Trends in Genetics, vol. 24, No. 3, Feb. 11, 2008, 9 pp.
Feuk et al., "Structural variation in the human genome," Nature Reviews | Genetics, vol. 7, Nature Publishing Group, Feb. 2006, 13 pp.
Eichler et al., "An Assessment of the Sequence Gaps: Unfinished Business in a Finished Human Genome," Nature Reviews | Genetics, vol. 5, May 2004, 10 pp.
Treangen et al., "Repetitive DNA and next-generation sequencing: computational challenges and solutions," Nature Reviews | Genetics, vol. 13, Macmillian Publishers Limited, Jan. 2012, 11 pp.
Howorka et al., "Sequence-specific detection of individual DNA strands using engineered nanopores," Nature Biotechnology, vol. 19, Nature Publishing Group, Jul. 2001, 4 pp.

Schwartz et al., "Separation of Yeast Chromosome-Sized DNAs by Pulsed Field Gradient Gel Electrophoresis," Cell, vol. 37, May 1984, 9 pp.
Oana et al., "Non-destructive handling of individual chromatin fibers isolated from single cells in a microfluidic device utilizing an optically driven microtool," Royal Society of Chemistry, Lab Chip, vol. 14, Nov. 21, 2013, 10 pp.
Benitez et al., "Microfluidic extraction, stretching and analysis of human chromosomal DNA from single cells," Royal Society of Chemistry, Lab Chip, vol. 12, Sep. 10, 2012, 7 pp.
Paegel et al., "Microfluidic devices for DNA sequencing: sample preparation and electrophoretic analysis," Current Opinion in Biotechnology, vol. 14, (Applicant points out, in accordance with MPEP 609.04(a), that the year of publication, 2003, is sufficiently earlier than the effective U.S. filing date, so that the particular month of publication is not in issue.), 9 pp.
Hilz et al., "Stimulation of Proteinase K Action by Denaturing Agents: Application to the Isolation of Nucleic Acids and the Degradation of 'Masked' Proteins," European Journal of Biotechnology, vol. 56, Mar. 14, 1975, 6 pp.
Brahmasandra et al., "Electrophoresis in microfabricated devices using photopolymerized polyacrylamide gels and electrode-defined sample injection," Electrophoresis, vol. 22, (Applicant points out, in accordance with MPEP 609.04(a), that the year of publication, 2001, is sufficiently earlier than the effective U.S. filing date, so that the particular month of publication is not in issue.), 12 pp.
Underhill et al., "DNA stretch during electrophoresis due to a step change in mobility," The American Physical Society, Physical Review E, vol. 76, Jul. 19, 2007, 7 pp.
Maydan et al., "Electrophoretic High Molecular Weight DNA Purification Enables Optical Mapping," Boreal Genomics, Inc., Journal of Biomolecular Techniques, vol. 24, Supplement, May 2013, 1 pp.
Dimalanta et al., "A Microfluidic System for Large DNA Molecule Arrays," American Chemical Society, Analytical Chemistry, vol. 76, No. 18, Sep. 15, 2004, 9 pp.
Berlin et al., "Assembling large genomes with single-molecule sequencing and locality-sensitive hashing," Nature Biotechnology, vol. 33, No. 6, Jun. 2015, 12 pp.
Gabrieli et al., "Genome-wide epigenetic profiling of 5-hydroxymethylcytosine by long-read optical mapping," Cold Spring Harbor Laboratory, bioRxiv The Reprint Server for Biology, Feb. 5, 2018, 20 pp.
Prinz et al., "Bacterial chromosome extraction and isolation," Royal Society of Chemistry, Lab Chip, vol. 2, Nov. 7, 2002, 6 pp.
Yu et al., "Tunable Confinement for Bridging Single-Cell Manipulation and Single-Molecule DNA Linearization," Small Journal, vol. 14, Mar. 25, 2018, 8 pp.
Marie et al., "Single-molecule DNA-mapping and whole-genome sequencing of individual cells," Proceedings of the National Academy of Sciences, vol. 115, No. 44, Oct. 30, 2018, 6 pp.
Murtaza et al., "Non-invasive analysis of acquired resistance to cancer therapy by sequencing of plasma DNA," Nature, vol. 497, Macmillan Publishers Limited, May 2, 2013, 6 pp.
Xia et al., "Soft Lithography," Angewandte Chemie International Edition, vol. 37, (Applicant points out, in accordance with MPEP 609.04(a), that the year of publication, 1998, is sufficiently earlier than the effective U.S. filing date, so that the particular month of publication is not in issue.), 26 pp.

* cited by examiner

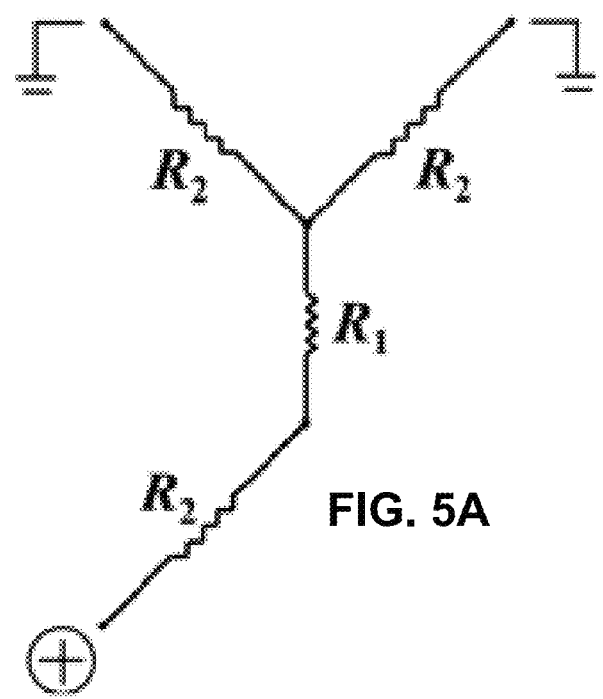
FIG. 5A
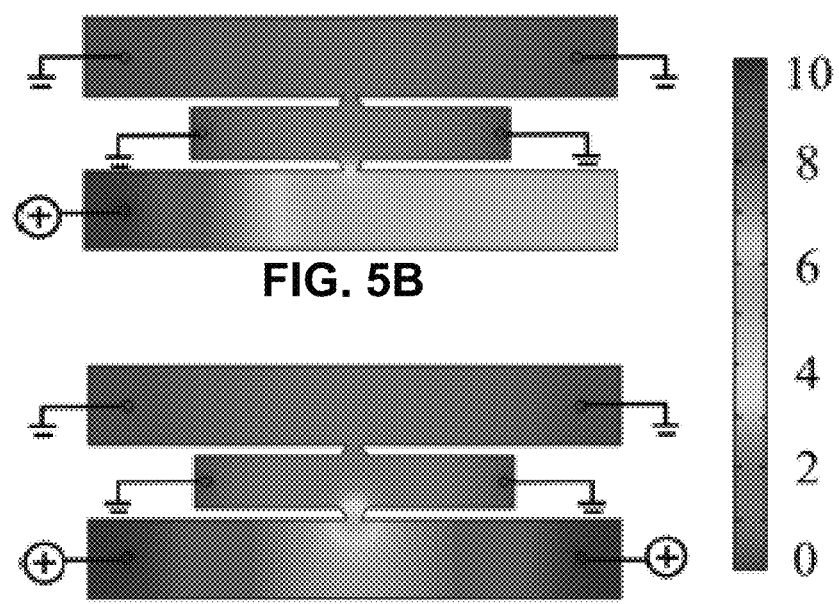
FIG. 5B
FIG. 5C

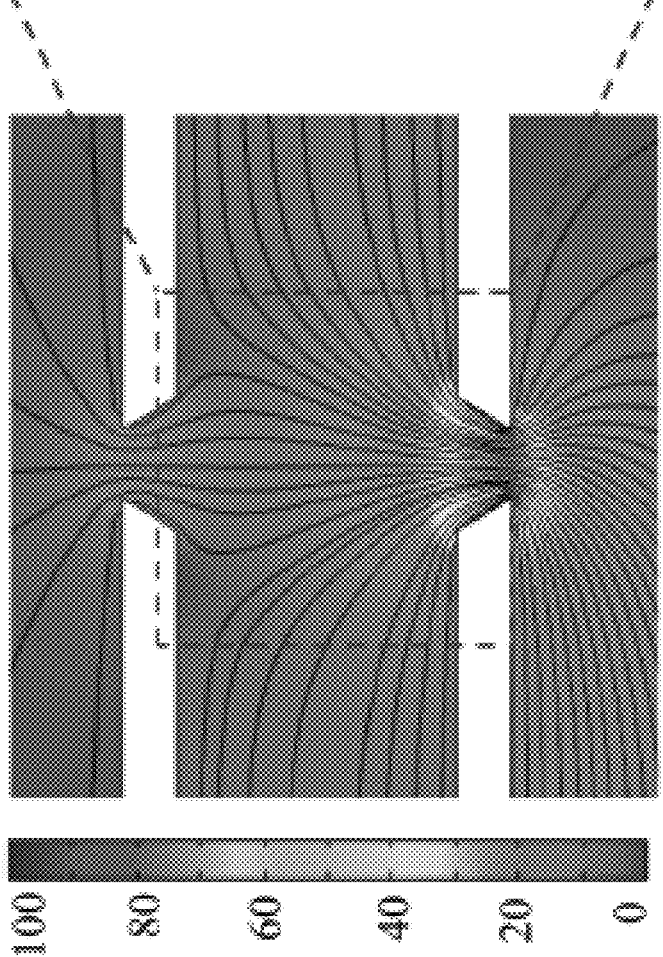
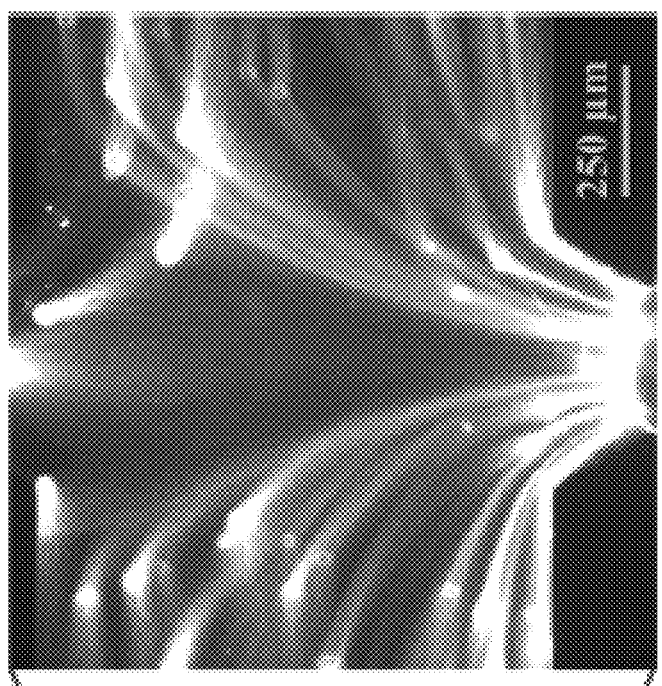
FIG. 6A
FIG. 6B

DNA EXTRACTION DEVICE

RELATED APPLICATIONS

This application claims the benefit of priority to U.S. Provisional Patent Application No. 62/657,395, filed Apr. 13, 2018, the entire content of which is incorporate by reference.

GOVERNMENT RIGHTS

This invention was made with government support under R21-HG009208 awarded by National Institutes of Health. The government has certain rights in the invention.

TECHNICAL FIELD

The disclosure relates to techniques and devices for extracting DNA from cells.

BACKGROUND

Genome mapping and sequencing technologies principally operate at nano/micro-scale and efficient sample preparation is crucial for successful technologies, especially for genomic DNA. Long chain DNA molecules are of significant importance for genomic technologies such as long-read sequencing (typically >10 kilo-base pairs (kbp)) and whole-genome mapping (typically >150 kbp). One of the major challenges in long-read sequencing and whole-genome mapping is the inability to extract long DNA molecules from cells quickly and efficiently, and then to deliver the long DNA molecules to downstream technologies without product degradation via fragmentation.

BRIEF DESCRIPTION OF THE DRAWINGS

FIG. 5A is a conceptual diagram of an equivalent Kirchhoff circuit for transverse electrophoresis in an example DNA extraction device, in accordance with some examples of this disclosure.

FIGS. 5B and 5C are representations of COMSOL computations of electric potential drop in an example DNA extraction device for a single-anode and a double-anode configuration, respectively.

FIG. 6A is a representation of COMSOL computations of electric field lines for an applied voltage of 10 V to a single anode.

FIG. 6B is a fluorescent image of YOYO-stained whole genomic DNA, extracted from MCF-7 cells in the device, following the field lines during electrophoresis, experimentally demonstrating the COMSOL calculations shown in FIG. 6A.

SUMMARY

Figure 1A:
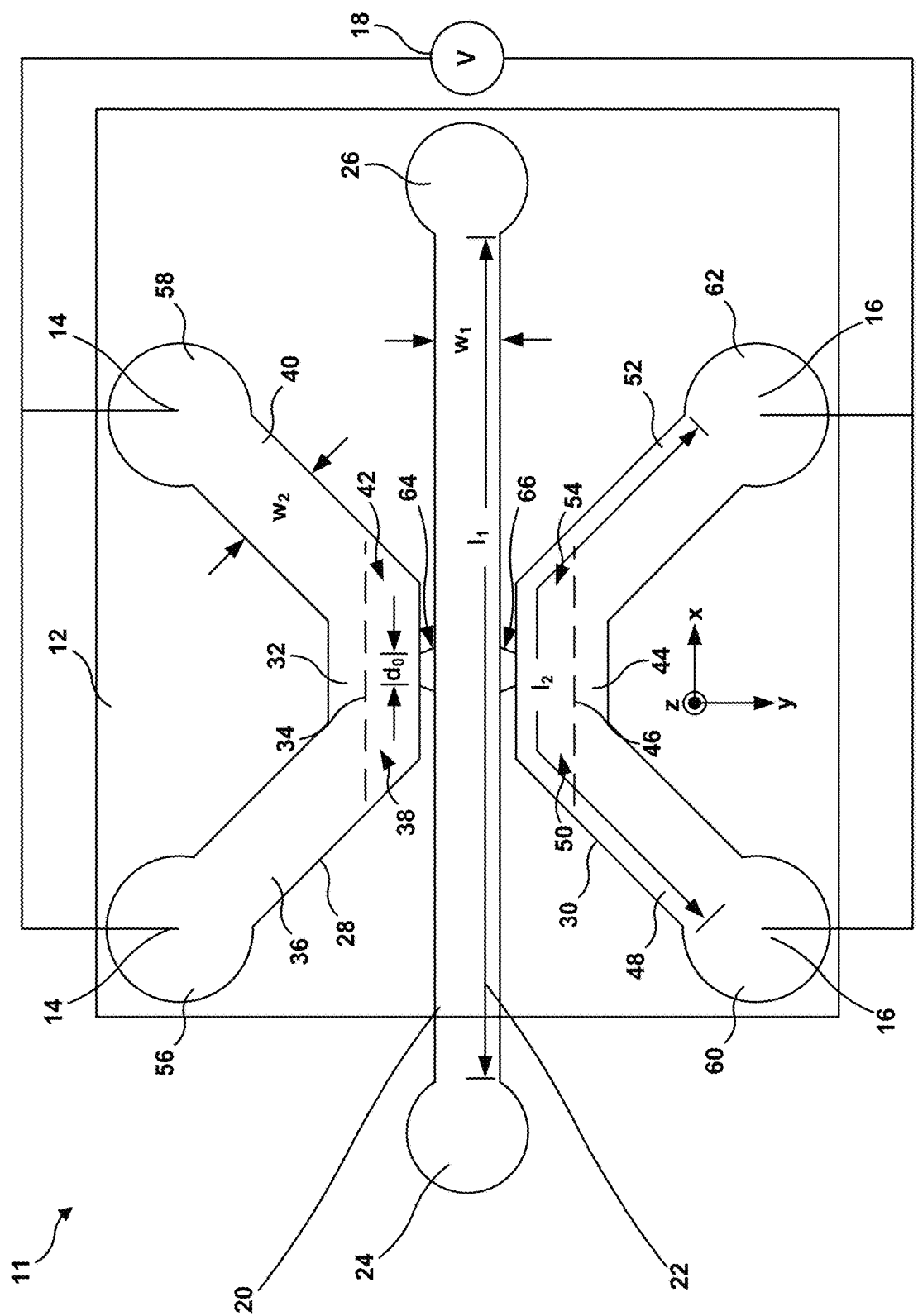
FIGS. 1A and 1B are conceptual diagrams illustrating example DNA extraction devices, in accordance with some examples of this disclosure.

In some examples, the disclosure describes a DNA extraction device that includes a substrate, at least one first side channel electrode, at least one second side channel electrode, and a voltage source connected between the at least one first side channel electrode and the at least one second side channel electrode. The substrate defines an elongate central channel defining a major axis. A width of the elongate central channel measured perpendicular to the major axis and in a major plane of the substrate is greater than a depth of the elongate central channel measured perpendicular to the major axis and perpendicular to the major plane of the substrate. A depth of the elongate central channel is less than about 15 times a diameter of a cell to be introduced in the elongate central channel. The substrate also defines a first side channel adjacent to the elongate central channel on a first side of the major axis and a second side channel adjacent to the elongate central channel on a second side of the major axis, where the second side is opposite the first side. The substrate further defines a first trapezoidally shaped connecting channel connecting the first side channel and the elongate central channel. A smaller parallel side of the first trapezoidally shaped connecting channel is open to the first side channel. The substrate additionally defines a second trapezoidally shaped connecting channel connecting the second side channel and the elongate central channel. A smaller parallel side of the second trapezoidally shaped connecting channel is open to the second side channel.

In some examples, the disclosure describes a method that includes introducing a gel and a cell sample in an elongate central channel of a DNA extraction device. The DNA extraction device includes a substrate, at least one first side channel electrode, at least one second side channel electrode, and a voltage source connected between the at least one first side channel electrode and the at least one second side channel electrode. The substrate defines an elongate central channel defining a major axis. A width of the elongate central channel measured perpendicular to the major axis and in a major plane of the substrate is greater than a depth of the elongate central channel measured perpendicular to the major axis and perpendicular to the major plane of the substrate. A depth of the elongate central channel is less than about 15 times a diameter of a cell to be introduced in the elongate central channel. The substrate also defines a first side channel adjacent to the elongate central channel on a first side of the major axis and a second side channel adjacent to the elongate central channel on a second side of the major axis, where the second side is opposite the first side. The substrate further defines a first trapezoidally shaped connecting channel connecting the first side channel and the elongate central channel. A smaller parallel side of the first trapezoidally shaped connecting channel open to the first side channel. The substrate additionally defines a second trapezoidally shaped connecting channel connecting the second side channel and the elongate central channel. A smaller parallel side of the second trapezoidally shaped connecting channel open to the second side channel. The method also includes introducing a cell lysis solution to at least one of the first side channel or the second side channel to cause the cell lysis solution to enter into the elongate central channel and lyse cells in the cell sample. The method further includes introducing an electrophoresis buffer solution to at least one of the first side channel or the second side channel to cause the electrophoresis buffer solution to enter into the elongate central channel. Additionally, the method includes placing at least one first side channel electrode in the first side channel and at least one second side channel electrode in the second side channel, and applying a voltage between the at least one first side channel electrode and the at least one second side channel electrode to accumulate DNA from the cell sample into at least one of the first side channel or the second side channel.

The details of one or more examples are set forth in the accompanying drawings and the description below. Other features, objects, and advantages of the disclosure will be apparent from the description and drawings, and from the claims.

DETAILED DESCRIPTION

In general, the disclosure describes a DNA extraction device into which a cell sample is introduced and from which a DNA sample is obtained. In some example, the DNA sample may include relatively long-chain DNA molecules, such as DNA molecules having greater than about 100 kilo-base pairs (kbp). The DNA extraction device may include three channels. The elongate central channel may be joined to each of the side channels by a respective trapezoidally shaped connecting channel. The cell sample may be placed in the elongate central channel in a gel (e.g., a gel for gel electrophoresis such as silica gel, agarose, polyacrylamide, starch, collagen, or the like). The lysis solution, a wash solution, and a gel electrophoresis solution may be introduced at different times (e.g., serially) to at least one of the side channels and enter into the elongate central channel.

The DNA extraction device also may include at least one first side channel electrode, at least one second side channel electrode, and, optionally, at least one elongate central channel electrode. During gel electrophoresis, the at least one first side channel electrode may be positioned in the first side channel, the at least one second side channel electrode may be positioned in the second side channel, and the at least one elongate central channel electrode optionally may be positioned in the elongate central channel. A voltage source may apply a voltage between the at least one first side channel electrode and the at least one second side channel electrode and, if present, the at least one elongate central channel electrode. This causes electrophoretic migration of the DNA obtained from the lysed cells in a direction transverse and/or parallel to the long axis of the elongate central channel. The DNA is driven through at least one of the first or second trapezoidally shaped connecting channels to a corresponding at least one of the first or second side channel, where the DNA may be collected. In this way, the same device may be used for cell lysis and DNA collection.

To facilitate lysing of the cells, the elongate central channel may define a depth that is greater than a diameter of the cells and less than about 15 times a diameter of the cells. The width of the elongate central channel is greater than the depth of the elongate central channel. Similarly, a width of a smaller parallel end of the trapezoidally shaped connecting channels is greater than a depth of the trapezoidally shaped connecting channels. This may provide relatively high cross-sectional area for movement of solutions between the channels while reducing a depth of the device, which may facilitate lysing of cells compared to devices that include channels that are relatively deeper.

The relative dimensions of the channels and trapezoidally shaped connecting channels are also configured to shape the electric field generated by the voltage source to focus the voltage drop across the trapezoidally shaped connecting channels. This may facilitate more efficient electrophoretic extraction of DNA from the elongate central channel into the at least one side channel.

FIG. 1A is a conceptual diagram illustrating an example DNA extraction device 10, in accordance with some examples of this disclosure. DNA extraction device 10 includes a substrate 12, at least one first side channel electrode 14, at least one second side channel electrode 16, and a voltage source 18 connected between at least one first side channel electrode 14 and at least one second side channel electrode 16. Substrate 12 defines an elongate central channel 20, a first side channel 28, a second side channel 30, a first trapezoidally shaped connecting channel 64 and a second trapezoidally shaped connecting channel 66.

Substrate 12 may be formed from any suitable material. In some examples, substrate 12 may be formed from a hydrophobic material, such as a hydrophobic polymeric material. A hydrophobic material may enable gel and cells to be retained in elongate central channel 20 while fluids (e.g., reagents and solutions) flow through side channels 28 and 30 and enter into elongate central channel 20. In some examples, the material from which substrate 12 is formed may be processable using lithography and/or molding techniques to form the relatively small-scale features in substrate 12. For example, substrate 12 may be formed from poly(dimethyl siloxane) (PDMS), poly(methyl methacrylate) (PMMA), cyclic olefin copolymer (COC), any hydrophobic polymeric material suitable for thermal imprinting, any hydrophobic polymeric material suitable for photo imprinting, any hydrophobic polymeric material suitable for hot embossing, or any hydrophobic polymeric material suitable for injection molding. Substrate 12 may also be formed in fused silica, borosilicate, silicon, or any hard material used for microfabrication that can be chemically treated to provide a hydrophobic surface.

Substrate 12 defines an elongate central channel 20 defining a major axis 22. A width $w_1$ of elongate central channel 20 measured perpendicular to major axis 22 and in a major plane of substrate 12 is greater than a depth of elongate central channel 20 measured perpendicular to major axis 22 and perpendicular to the major plane of substrate 12 (e.g., into the plane of FIG. 1). Such a configuration in which a depth of elongate central channel 20 is less than a width of elongate central channel 20 may facilitate lysing of cells in elongate central channel 20 by providing sufficient surface area for lysing solution to access the cells while reducing a cross-sectional area of elongate central channel 20 (in a plane normal to major axis 22).

The depth of elongate central channel 20 is greater than the diameter of cells to be introduced in elongate central channel 20. In some examples, the depth of elongate central channel 20 is less than about fifteen times the diameter of cells to be introduced in elongate central channel 20, or less than about ten times the diameter of cells to be introduced in elongate central channel 20, or less than about five times the diameter of cells to be introduced in elongate central channel 20.

Elongate central channel 20 may include a first port 24 and a second port 26. First port 24 may act as an inlet to elongate central channel 20 and second port 26 may act as an outlet to elongate central channel 20, or vice versa. For example, cells and gel may be introduced to elongate central channel 20 through first port 24, second port 26, both, or all along the length of elongate central channel 20. The diameter of first and second ports 24 may be between about 1 mm and about 5 mm, such as about 2 mm.

The length of elongate central channel 20, $l_1$, is defined between first port 24 and second port 26 (e.g., not including first port 24 and second port 26). The length of elongate central channel 20, $l_1$, may be selected based on one or more of a variety of factors. For example, the length of elongate central channel 20, $l_1$, affects the volume of material that can be contained in elongate central channel 20 (along with the width, $w_1$, and the depth of elongate central channel 20). As another example, the length of elongate central channel 20, $l_1$, affects the hydraulic resistance experienced during gel loading into the elongate central channel.

In some examples, the depth, width, and length of elongate central channel 20 may differ by an order of magnitude or more. For example, the depth of elongate central channel 20 may be between about 0.05 mm and about 0.2 mm, such as about 0.1 mm; the width, $w_1$, of elongate central channel 20 may be between about 0.5 mm and about 5 mm, such as about 1 mm, and the length, $l_1$, of elongate central channel 20 may be between about 5 mm and about 30 mm, such as about 6 mm or about 15 mm. In some examples, to scale DNA extraction device 10 to a different size, the ratios between the depth, width, and length of elongate central channel 20 may be kept within a range to result in a desired voltage drop profile within portions of DNA extraction device 10, and also within a range to result in desired hydraulic resistance of the elongate central channel for convenient gel or fluid loading. For example, the ratios between the depth, width, and length of elongate central channel 20 may be kept approximately constant.

Substrate 12 also defines a first side channel 28 adjacent to elongate central channel 20 on a first side of major axis 22 and a second side channel 30 adjacent to elongate central channel 20 on a second side of major axis 22. The second side is opposite the first side. First side channel 28 may include a central portion 32 defining a first side channel major axis 34 extending generally parallel to major axis 22 of elongate central channel 20, a first end portion 36 extending from a first end 38 of central portion 32 and diverging from major axis 22 of elongate central channel 20, and a second end portion 40 extending from a second end 42 of central portion 32 and diverging from major axis 22 of elongate central channel 20. Second side channel 30 similarly may include a central portion 44 defining a second side channel major axis 46 extending generally parallel to major axis 22 of elongate central channel 20, a first end portion 48 extending from a first end 50 of central portion 44 and diverging from major axis 22 of elongate central channel 20, and a second end portion 52 extending from a second end 54 of central portion 44 and diverging from major axis 22 of elongate central channel 20.

Each of first side channel 28 and second side channel 30 may include optional end ports. First side channel 28 may include a first end port 56 and a second end port 58. First end port 56 is fluidically coupled to first end portion 36 of first side channel 28 and second end port 58 is fluidically coupled to second end portion 40 of first side channel 28. Second side channel 30 may include a first end port 60 and a second end port 62. First end port 60 is fluidically coupled to first end portion 48 of second side channel 30 and second end port 62 is fluidically coupled to second end portion 52 of second side channel 30. End ports 56, 58, 60, and 62 may function as inputs, outputs, reservoirs, or combinations thereof for reagents and solutions to be introduced to first side channel 28 and second side channel 30. End ports 56, 58, 60, and 62 also may be configured to receive a respective one of at least one first side channel electrode 14 or at least one second side channel electrode 16. The diameter of end ports 56, 58, 60, and 62 may be between about 1 mm and about 5 mm, such as about 3 mm.

In some examples, first side channel 28 and second side channel 30 may define the same depth (measured in the z-axis of FIG. 1) as elongate central channel 20. For example, first side channel 28 and second side channel 30 may define a depth of between about 0.05 mm and about 0.3 mm, such as about 0.1 mm.

First side channel 28 and second side channel 30 each define a width, $w_2$. The width, $w_2$, of first side channel 28 and second side channel 30 may be the same or different. In some examples, the width, $w_2$, of first side channel 28 and second side channel 30 is between about 0.2 mm and about 5 mm, such as about 1.5 mm. In some examples, the width, $w_2$, of first side channel 28 and second side channel 30 is greater than the width, $w_1$, of elongate central channel 20.

First side channel 28 and second side channel 30 each define a length, $l_2$. The length, $l_2$, of first side channel 28 and second side channel 30 is defined from the first port to the second port and does not include the size of the ports. The length, $l_2$, of first side channel 28 and second side channel 30 may be the same or different. In some examples, the length, $l_2$, of first side channel 28 and second side channel 30 is between about 5 mm and about 50 mm, such as about 10 mm. In some examples, the width, $w_2$, of first side channel 28 and second side channel 30 is less than the width, $w_1$, of elongate central channel 20.

Substrate 12 further defines a first trapezoidally shaped connecting channel 64 connecting first side channel 28 and elongate central channel 20 and a second trapezoidally shaped connecting channel 66 connecting second side channel 30 and elongate central channel 20. A smaller parallel side of first trapezoidally shaped connecting channel 64 opens to first side channel 28 and a larger parallel side of first trapezoidally shaped connecting channel 64 opens to elongate central channel 20. Similarly, a smaller parallel side of second trapezoidally shaped connecting channel 66 opens to second side channel 30 and a larger parallel side of second trapezoidally shaped connecting channel 66 opens to elongate central channel 20.

A width, $d_0$, of the smaller parallel side of first trapezoidally shaped connecting channel 64 and second trapezoidally shaped connecting channel 66 may be greater than the depth of elongate central channel 20. For example, the width, $d_0$, of the smaller parallel side of first trapezoidally shaped connecting channel 64 and second trapezoidally shaped connecting channel 66 may be between 0.1 mm and about 0.7 mm, such as about 0.25 mm. The width, $d_0$, of the smaller parallel side of first trapezoidally shaped connecting channel 64 and second trapezoidally shaped connecting channel 66 may be sufficient to provide relatively high cross-sectional area for fluids (e.g., reagents and solutions) to enter from first side channel 28 and second side channel 30 to elongate central channel 20, while reducing or substantially preventing movement of gel or cells from elongate central channel 20 to first side channel 28 or second side channel 30. Further, the internal angle of first trapezoidally shaped connecting channel 64 and second trapezoidally shaped connecting channel 66 may be selected such that the internal angle, in combination with the contact angle of the material of substrate 12 is sufficient to help retain cells and gel within elongate central channel 20. For example, an internal angle of each of first trapezoidally shaped connecting channel 64 and second trapezoidally shaped connecting channel 66 may be greater than 30° and less than 90°, such as about 60°.

At least one first side channel electrode 14 and at least one second side channel electrode 16 are electrically coupled to first side channel 28 and second side channel 30, respectively. At least one first side channel electrode 14 and at least one second side channel electrode 16 are also electrically coupled to voltage source 18. In this way, at least one first side channel electrode 14 and at least one second side channel electrode 16 enable voltage source 18 to apply a voltage transversely across DNA extraction device 10 (e.g., in a direction generally perpendicular to the orientation of major axis 22 of elongate central channel 20).

In some examples, at least one first side channel electrode 14 and at least one second side channel electrode 16 enable voltage source 18 may be permanently attached to substrate 12. In other examples, at least one first side channel electrode 14 and at least one second side channel electrode 16 may be removably coupled to substrate 12 to allow at least one first side channel electrode 14 and at least one second side channel electrode 16 to enable voltage source 18 to be disconnected from substrate 12 during selected steps of use of DNA extraction device 10 (e.g., during cell lysis) and present during other steps of use of DNA extraction device 10 (e.g., during electrophoresis). At least one first side channel electrode 14 and at least one second side channel electrode 16 enable voltage source 18 may include any suitable electrically conductive material, e.g., an electrically conductive material that is substantially inert relative to the fluids and solutions that at least one first side channel electrode 14 and at least one second side channel electrode 16 enable voltage source 18 contact. In some examples, at least one first side channel electrode 14 and at least one second side channel electrode 16 enable voltage source 18 include platinum or a platinum alloy.

At least one first side channel electrode 14 and at least one second side channel electrode 16 enable voltage source 18 may include a single electrode disposed in first side channel 28 and a single electrode disposed in second side channel 30 or may include more than one electrode disposed in first side channel 28, second side channel 30, or both. For example, as shown in FIG. 1A, at least one first side channel electrode 14 includes two first side channel electrodes, one first side channel electrode positioned in first end port 56 at an end of first end portion 36 of first side channel 28 and one first side channel electrode positioned in second end port 58 at an end of second end portion 40 of first side channel 28. Similarly, at least one second side channel electrode 16 includes two second side channel electrodes, one second side channel electrode positioned in first end port 60 at an end of first end portion 48 of second side channel 30 and one second side channel electrode positioned in second end port 62 at an end of second end portion 52 of second side channel 30. Using more than one first side channel electrode 14 and more than one second side channel electrode 16 may facilitate control of the shape and contour of the electric field within elongate central channel 20, first side channel 28, second side channel 30, first trapezoidally shaped connecting channel 64, and second trapezoidally shaped connecting channel 66 that is generated upon application of the voltage between at least one first side channel electrode 14 and at least one second side channel electrode 16. For example, controlling a position of each of the at least one first side channel electrode 14 within first side channel 28 and a position of each of the at least one second side channel electrode 16 within second side channel 30 allows control of the shape and contour of the electric field within elongate central channel 20, first side channel 28, second side channel 30, first trapezoidally shaped connecting channel 64, and second trapezoidally shaped connecting channel 66.

Figure 1B:
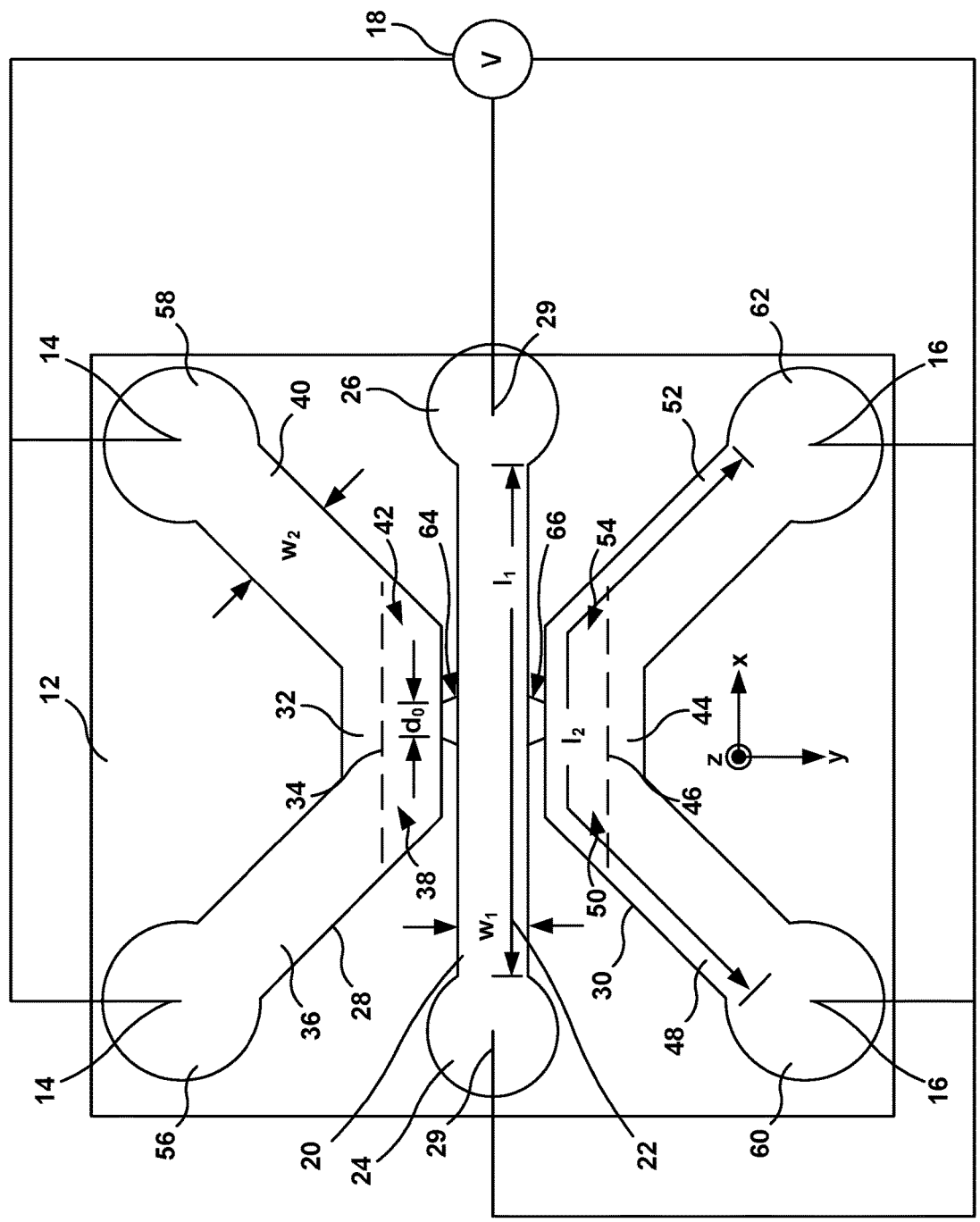

In some examples, as shown in FIG. 1B, an example DNA extraction device 11 may include at least one elongate central channel electrode 29. In the example shown in FIG. 1B, DNA extraction device 11 includes two elongate central channel electrodes 29, one electrode disposed in each of first port 24 and second port 26. Elongate central channel electrodes 28 may enable further control of the shape and contour of the electric field within elongate central channel 20, first side channel 28, second side channel 30, first trapezoidally shaped connecting channel 64, and second trapezoidally shaped connecting channel 66. Example DNA extraction device 11 also include a shorter elongate central channel 20 than DNA extraction device 10. All other aspects of DNA extraction device 11 may be the same as or similar to DNA extraction device 10.

Additionally or alternatively, electrodes 14, 16, and, if present, 29, may be controllably connectable to voltage source 18, and may be connected differently at different points within the DNA extraction technique. For example, during a first portion of a DNA extraction technique, first side channel electrodes 14 may be connected to ground, along with optional elongate central channel electrodes 29. During the first portion of the DNA extraction technique, second side channel electrode 16 in first end port 60 may be connected as an anode, and second side channel electrode 16 in second end port 62 may be left at a floating voltage. During a second portion of a DNA extraction technique, first side channel electrodes 14, along with optional elongate central channel electrodes 29, may be left floating; second side channel electrode 16 in first end port 60 may be connected as an anode, and second side channel electrode 16 in second end port 62 may be connected to ground. Other configurations of electrode connections to voltage source 18 are also possible depending upon the flow direction of DNA desired.

Voltage source 18 may include any suitable voltage source, for example a DC voltage source or an AC voltage source. Voltage source 18 outputs an electrical signal with selected signal parameters, including duration, amplitude, frequency, and the like. In some examples, voltage source 18 may be configured or controlled to output a pulsed DC voltage, a continuous DC voltage, or a continuous AC voltage.

The amplitude of the voltage may be selected based on geometry of DNA extraction device 10, e.g., based on lengths and cross-sectional areas of elongate central channel 20, first side channel 28, second side channel 30, first trapezoidally shaped connecting channel 64, and second trapezoidally shaped connecting channel 66. An upper bound of the voltage amplitude may be defined by damaging cells or DNA due to excessive Joule heating. A lower bound of the voltage amplitude may be defined by the time required to extract DNA from elongate central channel 20 during electrophoresis. In some examples, the voltage amplitude may be between about 1 volt and about 200 volts, such as about 10 volts or about 20 volts.

During use, elongate central channel 20 may be at least partially filled with a gel and a cell sample. The gel may include a cell lysis or electrophoresis gel, including, for example, an agarose, polyacrylamide, silica gel, starch, collagen, poly(ethylene oxide), or the like. The cell sample may include any suitable cells, including, for example, mammalian cells, plant cells, microorganisms, or the like.

Figure 2:
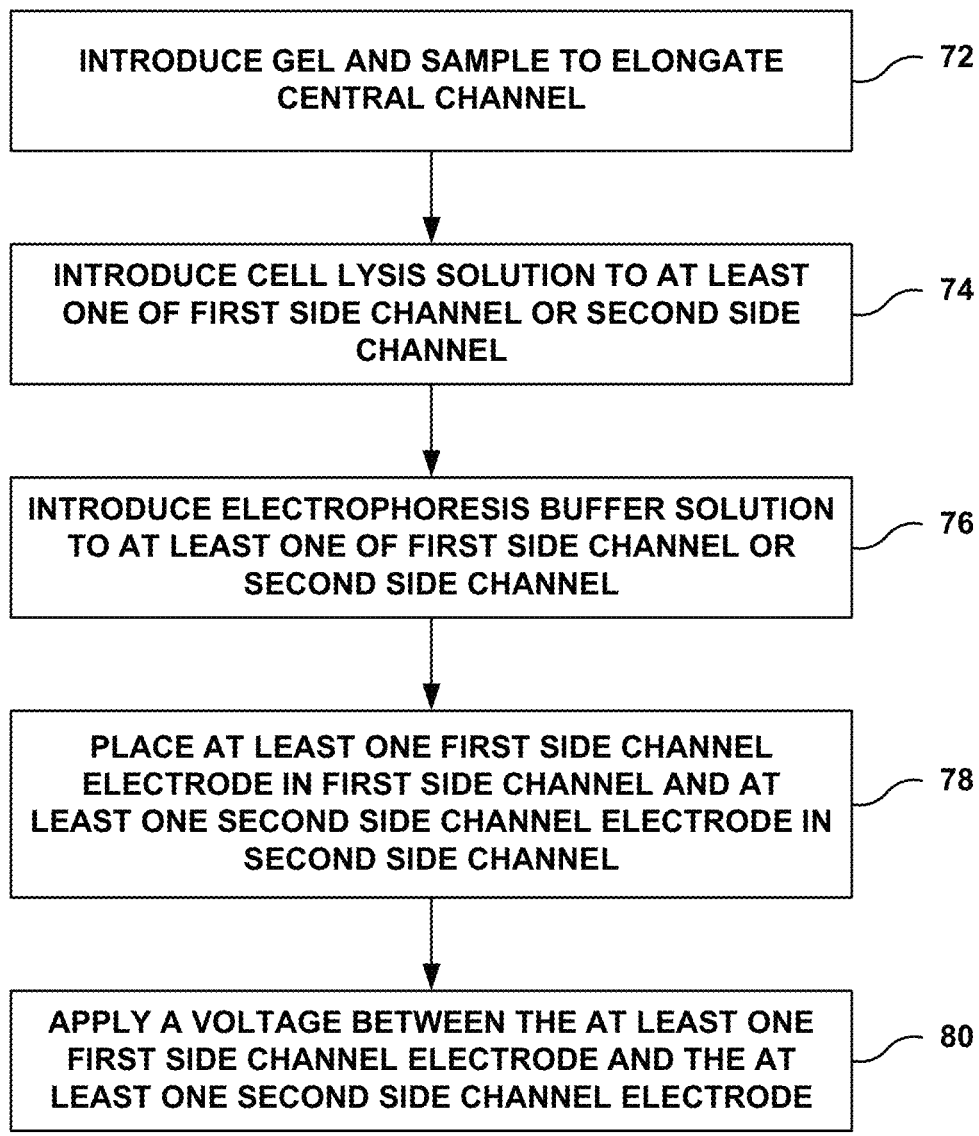
FIG. 2 is a flow diagram illustrating an example technique for extracting DNA from cells, in accordance with some examples of this disclosure.

FIG. 2 is a flow diagram illustrating an example technique for extracting DNA from cells, in accordance with some examples of this disclosure. The technique of FIG. 2 will be described with concurrent reference to DNA extraction device 10 of FIG. 1. First, a gel and a cell sample may be introduced in elongate central channel 20 of DNA extraction device 10 (72). As described above, a depth of elongate central channel 20 (e.g., as measured in the z-axis of FIG. 1) may be between a diameter of the cells in the cell sample and about 15 times a diameter of the cells in the cell sample.

The method also includes introducing a cell lysis solution to at least one of first side channel 28 or second side channel 30 to cause the cell lysis solution to enter into elongate central channel 20 and lyse cells in the cell sample (74).

The method may optionally include introducing a wash solution to at least one of first side channel 28 or second side channel 30 to cause the wash solution to enter into elongate central channel 20 to remove lysed cellular material, e.g., into at least one of side channel 28 or second side channel 30.

The method further includes introducing an electrophoresis buffer solution to at least one of first side channel 28 or second side channel 28 to cause the electrophoresis buffer solution to enter into elongate central channel 20 (76). For example, the electrophoresis buffer solution may be introduced to at least one of ports 56, 58, 60, or 62. The electrophoresis buffer solution may include, for example, Tris/Acetate/ethylenediaminetetraacetic acid (EDTA) (TAE), Tris/Borate/EDTA (TBE), or any other suitable electrophoresis buffer solution.

Additionally, the method may include placing at least one first side channel electrode 14 in first side channel 28, at least one second side channel electrode 16 in second side channel 30, and, optionally, at least one elongate central channel electrode 29 in elongate central channel 20 (78). As described above, in some examples, at least one first side channel electrode 14, at least one second side channel electrode 16, and optional at least one elongate central channel electrode 29 are attached to substrate 12 and are permanently in place in first side channel 28 and second side channel 30. In other examples, at least one first side channel electrode 14, at least one second side channel electrode 16, and optional at least one elongate central channel electrode 29 may be removable from substrate 12 and may be placed in first side channel 28, second side channel 30, and/or elongate central channel 20 prior to electrophoresis.

In some examples, to arrive at the configuration shown in FIG. 1, one first side channel electrode may be positioned in first end port 56 at an end of first end portion 36 of first side channel 28 and one first side channel electrode may be positioned in second end port 58 at an end of second end portion 40 of first side channel 28. Similarly, one second side channel electrode may be positioned in first end port 60 at an end of first end portion 48 of second side channel 30 and one second side channel electrode may be positioned in second end port 62 at an end of second end portion 52 of second side channel 30. Similarly, one elongate central channel electrode 29 may be placed in first port 24 and one elongate central channel electrode 29 may be placed in second port 26.

The method of FIG. 2 further includes applying a voltage between at least one first side channel electrode 14, at least one second side channel electrode 16, and, optionally, at least one elongate central channel electrode 29 to accumulate DNA from the cell sample into at least one of first side channel 28 or second side channel 30 (80). As described above, voltage source 18 may apply a DC voltage or an AC voltage between at least one first side channel electrode 14, at least one second side channel electrode 16, and, optionally, at least one elongate central channel electrode 29. The DC voltage may be a pulsed voltage, a continuous voltage, or any time-dependent voltage signal. The voltage may cause the DNA in elongate central channel 20 to migrate through one or both of first trapezoidally shaped connecting channel 64 or second trapezoidally shaped connecting channel 66 (depending on the sign of the voltage) into first side channel 28, second side channel 30, or both. The extracted DNA then can be collected from first side channel 28, second side channel 30, or both.

Figure 3:
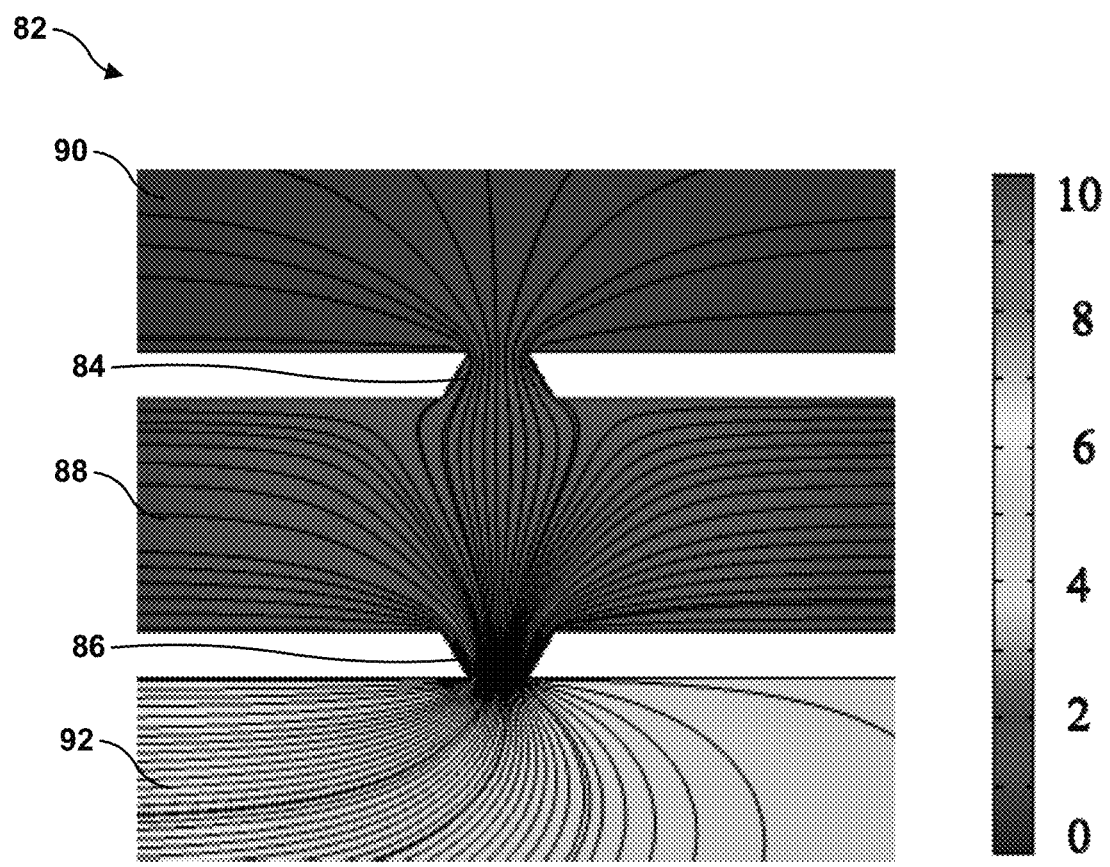
FIG. 3 is a conceptual diagram illustrating relative electrical potential and electric field lines for an example DNA extraction device, in accordance with some examples of this disclosure.

As mentioned above, the geometry of DNA extraction device 10, including the sizes and shapes of elongate central channel 20, first side channel 28, second side channel 30, first trapezoidally shaped connecting channel 64, and second trapezoidally shaped connecting channel 66, and the position of at least one first side channel electrode 14, at least one second side channel electrode 16, and, optionally, at least one elongate central channel electrode 29 are selected to control a shape and contour of the electric field generated by the applied voltage. For example, the geometry of DNA extraction device 10 may be selected to focus or concentrate the potential drop in first trapezoidally shaped connecting channel 64, second trapezoidally shaped connecting channel 66, or both. FIG. 3 is a conceptual diagram illustrating relative electrical potential and electric field lines for an example DNA extraction device 82, in accordance with some examples of this disclosure. As shown in FIG. 3, the potential drop is focused or concentrated in the trapezoidally shaped connecting channels 84 and 86 for faster DNA elution out of the central channel 88 while maintaining the gel in the central channel 88 during the various steps of operation of the DNA extraction device 82.

The preceding description has described a DNA extraction device including a single elongate central channel and associated side channels and trapezoidally shaped connecting channels. In some examples, a DNA extraction device may include multiple elongate central channels and associated side channels and trapezoidally shaped connecting channels on a single substrate. For example, multiple elongate central channels and associated side channels and trapezoidally shaped connecting channels may be disposed in parallel along the long axis of the DNA extraction device.

EXAMPLES

A silicon master mold was fabricated using standard photolithography with SU-8 2050 photoresist (available from MicroChem Corp., Westborough, Mass.) used to pattern the 100 µm deep channels. Devices were made by replica molding using degassed 10:1 poly(dimethylsiloxane) (PDMS) (SYLGARD™ 184, Dow Corning, Midland Mich.) and cured at 75° C. for 2 hours. Reservoirs were punched in the gel and fluid channels, and the devices were bonded to glass microscope slides after oxygen plasma treatment for 2 minutes. The devices were heated at 75° C. for 36 hours to completely restore the hydrophobicity of the PDMS.

Figure 4:
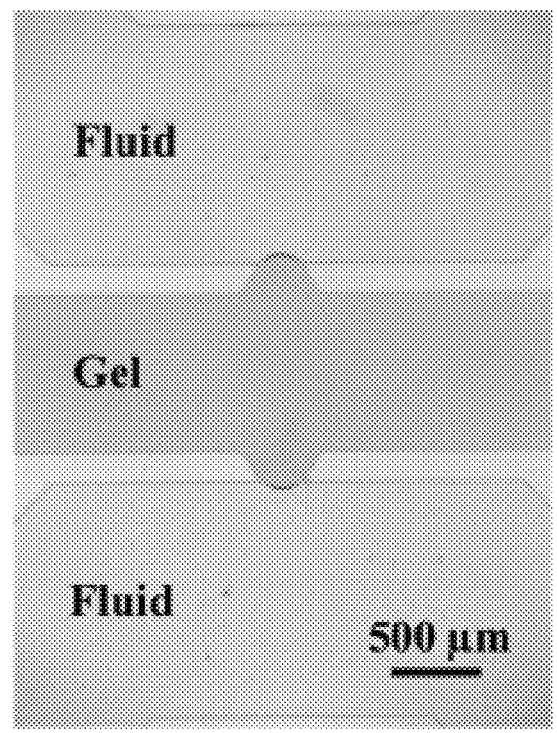
FIG. 4 is a microscope image of an example fabricated PDMS device, including trapezoidally shaped connecting channels and the central gel channel filled with orange-colored agarose, in accordance with some examples of this disclosure.

The DNA extraction PDMS device featured an elongate central gel microchannel for embedding cells and immobilizing DNA during lysis and sample purification steps, communicating with two parallel side channels on either side of the elongate central gel microchannel via the trapezoidally shaped connecting channels. The resulting device structure was like that shown in FIG. 1. The dimensions were as follows: $l_1$=6 mm, $w_1$=1 mm, $l_2$=10 mm, $w_2$=1.5 mm, $d_0$=250 µm, and channel depth=100 µm. The diameter of first port 24 and a second port 26 was 2 mm and the diameter of end ports 56, 58, 60, and 62 was 3 mm. FIG. 4 is a microscope image of the fabricated PDMS DNA extraction device, including the trapezoidally shaped connecting channels and the elongate central gel channel filled with orange-colored agarose. The trapezoidally shaped connecting channels facilitate diffusive molecular exchange between the gel and the fluid flowing through the side channels, and later aid in electrophoretic extraction. The design of the DNA extraction device included considering two aspects: (i) the hydrodynamic resistance during gel loading and fluid exchange; and (ii) the electric field strength in different parts of the device.

Balancing the hydrodynamic resistance during gel loading is important to keep the gel in the elongate central channel. This is achieved by contact line pinning, a physical principle previously exploited in microfluidic devices for 3D cell culture. Since PDMS is hydrophobic, a trapezoid-shaped communicating channel with a 60° angle supplements the PDMS-gel contact angle to establish a radius of curvature that provides a high Laplace pressure. To prevent gel from bursting into the fluid channel, the hydraulic pressure drop in the gel channel while loading agarose should not exceed the surface tension-sustained pressure differential at the agarose-air interface, where the latter depends on the radii of curvature in the z (along the device depth) and x (along the gel channel length) directions. This effect was achieved for 3D cell culture by choosing appropriate channel depth and trapezoid dimensions to obtain the required Laplace pressure. In the cell culture application, it is important to have deep channels to maintain three-dimensionality. For DNA extraction, in theory, the ultimate lower bound on channel depth is governed by the cell size. However, in practice, the resultant Laplace pressure also should be considered. Since this pressure is independent of the direction of gravity, the channel depth and trapezoid dimensions were interchanged so that similar gel caging is achievable as 3D cell culture using relatively shallow channels, which obviates the need to handle highly viscous photoresists during fabrication.

The extraction of DNA out of the gel is improved by employing electrophoresis both along (lateral) and across (transverse) the gel channel. Choosing a small gel length ($l_1$) reduces hydrodynamic resistance during gel loading, provides a high electric field along the gel for a given applied potential and ensures a small electrophoresis migration distance. To induce a high electric field in the overlapping region of the gel, the remaining channel dimensions can be chosen such that a significant potential drop occurs across the width of the gel. To achieve this, Kirchhoff's laws were used as a preliminary design step. The resistance R of a channel of length l and cross-sectional area A was estimated as $R=\sigma l/A$. The resistivity σ for the fluid and gel channels was approximated as equal because the gel is 99.8% buffer. Since all channels in the device have the same depth, the ratio of length to width of each section determines the relative resistances. The potential drop was calculated in the different channels along the transverse electrophoretic path by first considering an elementary resistor network shown in FIG. 5A, and then using a more accurate COMSOL model by including the lateral electrophoresis effects (FIGS. 5B and 5C).

The equivalent circuit has two parallel fluid channels in series with a gel and another fluid channel. The objective was to increase the gel resistance Rl relative to the other resistances in the equivalent circuit, and hence the potential drop across the gel. Apart from this, other noteworthy points during dimension selection were that (i) using wide ($w_2$) and short ($l_2$) fluid channels provides low resistance during continuous flow reagent exchange, and ensures a small potential drop in the fluid channels; (ii) a small gel width ($w_1$) ensures a small diffusion length and a small electrophoresis migration distance; and (iii) a small overlap length ($d_0$) equivalent to a single trapezoid communicating channel ensures uniform and almost straight electric field lines in the transverse direction, and provides a high gel resistance because it is the effective gel width during the electrical resistance calculation. Based on these considerations, an approximate working regime for all dimensions was identified by applying Kirchhoff and Ohm's laws to the equivalent circuit model, and a final set of dimensions was determined by modeling an equivalent geometry in COMSOL to study the potential drop and electric field lines. The gel channel length $l_1$ was ultimately adjusted to obtain similar electric field magnitude in both lateral and transverse electrophoresis directions in the gel. In the example 100 µm deep DNA extraction device, the elongate central gel channel had a length $l_1$=6 mm, width $w_1$=1 mm, and 2 mm diameter end ports. The fluid channels had a length $l_2$=10 mm, width $w_2$=1.5 mm, and 3 mm diameter ports. The trapezoidal short edge defining the overlap length is $d_0$=250 µm, with the longer parallel edge of the trapezoid being 500 µm.

The finite element calculation in COMSOL exhibited a strong electric field in the gel in both electrophoresis directions, for an applied voltage as little as 10 V, with almost straight field lines minimizing the electrophoretic path of DNA, as shown in FIG. 6A. FIG. 6B is a fluorescent image of YOYO-stained whole genomic DNA, extracted from MCF-7 cells in the device, following the field lines during electrophoresis, experimentally demonstrating the COMSOL calculations shown in FIG. 6A. The modeling also revealed a benefit of having one anode instead of two (comparing FIGS. 5B and 5C). While the potential drop across the gel is the same in the one anode and two anode cases, the electric field in the anodic fluid channel is stronger in the single anode configuration (FIG. 5B), leading to faster motion of DNA to the port. The single anode also drives all the DNA to one reservoir, rather than splitting the DNA yield into two streams, simplifying DNA recovery.

MCF-7 cells derived from human breast adenocarcinoma (ATCC HTB-22) were cultured at 37° C. and 5% $CO_2$ in a 24-well plate in high glucose Dulbecco's modified Eagle's medium (available from Sigma-Aldrich Corp., St. Louis, Mo.), supplemented with 10% fetal bovine serum (available from Thermo Fisher Scientific, Waltham, Mass.) and 1% penicillin-streptomycin (available from Thermo Fisher Scientific). After confluence, cells were trypsinized and centrifugally washed two times with 1× phosphate buffered saline (PBS) (available from Thermo Fisher Scientific). These $6×10^5$ cells were re-suspended in 200 μL PBS to produce a cell density of ~3000 cells per μL. 20 μL of this cell solution was pipette-mixed with 20 μL of molten 0.4 wt. % pulsed-field certified agarose (available from Bio-Rad Laboratories, Inc., Hercules, Calif.) prepared in 1×TBE buffer. The final 0.2 wt. % agarose mixture having a cell density of 1500 cells per μL was loaded into the elongate central gel channel using a pipette, avoiding spillage into the fluidic channel. The device was equilibrated at room temperature for 5 minutes, and then cooled at 4° C. for 30 seconds by placing it in a Petri dish to solidify the agar plug.

The cells were lysed diffusively at 37° C. for 1.5 hours by filling the two side channels with a detergent lysis solution 70 μL RIPA buffer (available from Thermo Fisher Scientific; 0.1% SDS), 10 μL pH 8 TE buffer (available from Thermo Fisher Scientific), 10 μL SDS lysis buffer (available from Sigma-Aldrich Corp.; 1% SDS), proteinase K (available from Qiagen, Hilden, Germany) at a concentration of 2 mg mL-1, and YOYO-1 (available from Thermo Fisher Scientific) at a concentration of 4 μM. The YOYO-1 is a cell membrane-impermeant DNA intercalating dye that is an illuminating component of the lysis solution. YOYO-1 fluoresces on the completion of cell lysis. Detergent in chemical lysis solutions causes cellular membrane degradation, which is instantaneous, and the small detergent molecules are not diffusion-limiting. While typical plug lysis protocols use stronger detergents (1% SDS), the choice of a milder detergent (0.17% SDS) was guided by the requirement of simultaneous YOYO-labeling, which is not effective in the presence of stronger detergents. The lysis temperature and the combination of buffers in the lysis solution were chosen for effective degradation of the proteins by proteinase K. After lysis, the cellular debris, digested proteins, and other salts and contaminants were allowed to diffuse out of the elongate central gel channel into the side channels, which were continuously replenished with fresh wash buffer (10 mM Tris-HCl pH 8, 50 mM EDTA) at about 4 μL min$^{-1}$ for 45 minutes, followed by TE buffer for 45 minutes. Since all contaminant molecules are smaller than the pore size for 0.2 wt. % agarose, effective washing of the gel was achieved by molecular diffusion. Moreover, continuous flow in the fluidic channels facilitated immediate elimination of the cellular waste once it diffused to the gel-fluid interface.

Figure 7B:
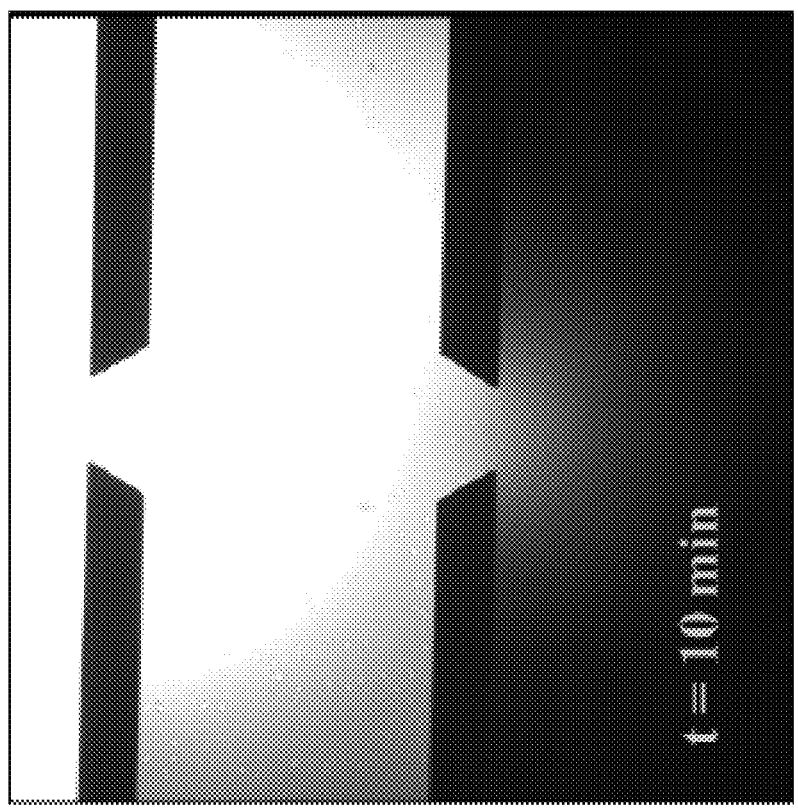
FIGS. 7A and 7B and microscope images illustrating diffusion of fluorescein through agarose gel and MCF-7 cells.
Figure 7A:
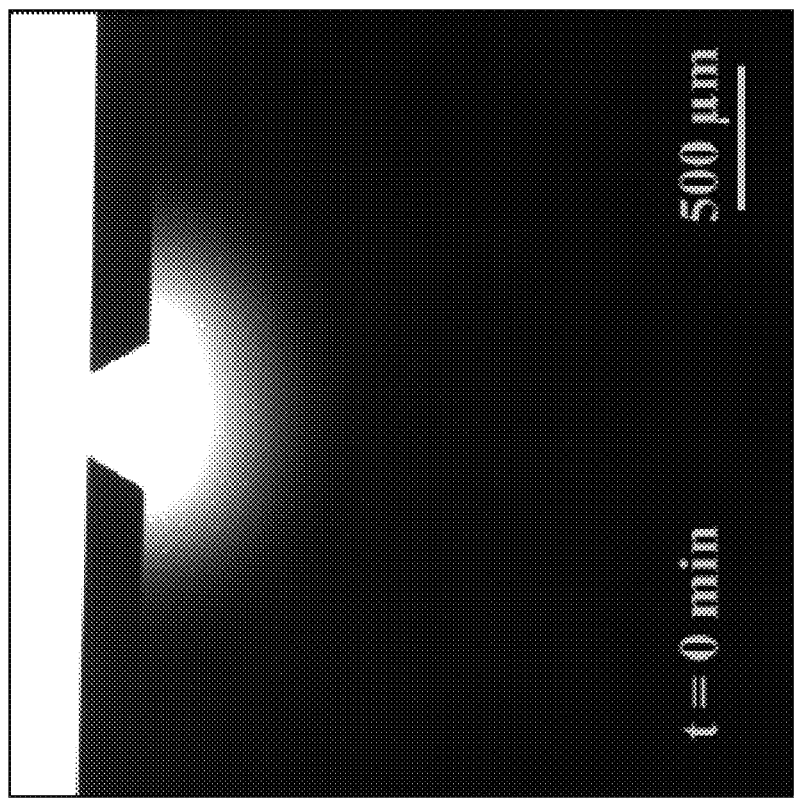

The time required for cell lysis and sample purification is based on the diffusion of different reagent molecules through the gel. To estimate this time, a control experiment was performed to characterize the diffusion of fluorescein across the elongate central gel channel when loaded with MCF-7 cells embedded in agarose, as shown in FIGS. 7A and 7B. From the experimental image at t=10 min (FIG. 7B), it can be seen that fluorescein radially diffuses 1.5 mm to the bottom channel through the gel. To reach the reservoirs, the molecule migrates 3 mm in either direction in the gel. However, during cell lysis and DNA purification, both fluid channels are filled with the reagent of interest, and the migration distance is reduced by a factor of 2. The biggest molecule in the lysis solution is Proteinase K (MW=18.5 kDa). The diffusivity of a larger 40 kDa growth factor in less porous Type I collagen at 37° C. is D=$5×10^{-11}$ $m^2$/s. By correcting for the difference in diffusivity, migration length and boundary conditions, a lysis time of <90 minutes was obtained. Based on this conservative estimate, the lysis time is chosen to be 1.5 hours to ensure complete protein digestion in the entire gel. It was assumed that peptide sizes after protease digestion are similar to fluorescein, since Proteinase K cleaves human histone H3.1 (MW=15404 g/mol) at 67 sites, with the largest peptide mass being 828 Da (analyzed by PeptideCutter tool from UniProt). The digested proteins and cellular debris are quickly eliminated from the gel. However, to completely remove Proteinase K from the gel, the washing time was also selected as 1.5 hours.

Figure 8A:
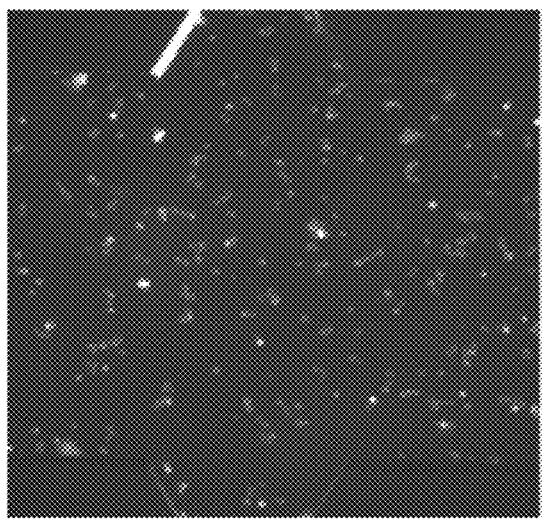
FIG. 8A is a bright-field image of transfected cells with 2B-GFP-labelled histones before cell lysis.
Figure 8B:
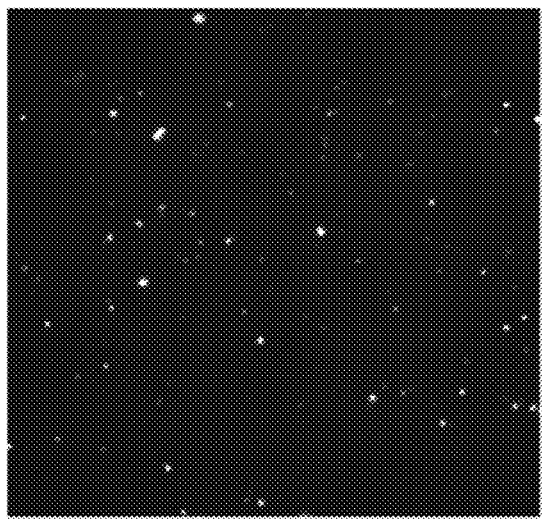
FIG. 8B is a fluorescent image of transfected cells with 2B-GFP-labelled histones before cell lysis.
Figure 8C:
FIG. 8C is a bright-field image of transfected cells with 2B-GFP-labelled histones after the 1.5-hour cell lysis step.
Figure 8D:
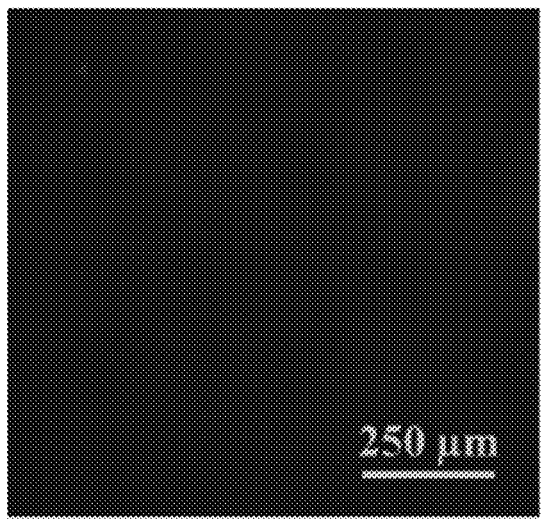
FIG. 8D is a fluorescent image of transfected cells with 2B-GFP-labelled histones after the 1.5-hour cell lysis step.

The results of this experiment allowed scaling up of the lysis time using the diffusivity of proteinase K, which is the biggest molecule in the lysis solution, based on the inverse dependence of process time on the diffusivity of the molecule. The sample purification time was estimated similarly to remove all the proteinase K from the gel after its role in protein digestion was complete. While completion of cell lysis was marked by illumination of the DNA by YOYO, complete digestion of histones by proteinase K also was verified in a separate experiment by measuring the fluorescence of histones in Histone 2B-GFP transfected cells before and after cell lysis using the lysis protocol described above (FIGS. 8A-8D). For cell transfection and selective labeling of histone 2B with GFP, 15 μL of CellLight Histone 2B-GFP, BacMam 2.0 construct (available Thermo Fisher Scientific) was added to 50,000 cells in a 24-well plate and incubated for 16 hours. Cells were then washed, mixed with agarose and seeded in the device. These cells were lysed for 1.5 hours at 37° C. using the lysis solution described above without YOYO. FIG. 8A is a bright-field image of transfected cells with 2B-GFP-labelled histones before cell lysis. FIG. 8B is a fluorescent image of transfected cells with 2B-GFP-labelled histones before cell lysis. FIG. 8C is a bright-field image of transfected cells with 2B-GFP-labelled histones after the 1.5-hour cell lysis step. FIG. 8D is a fluorescent image of transfected cells with 2B-GFP-labelled histones after the 1.5-hour cell lysis step.

In the miniaturized gel, the electric field is strong even for low applied potentials (FIG. 6A). This helps to accomplish fast electrophoretic extraction of DNA without encountering high voltage ramifications like fluid evaporation from the reservoirs or Joule heating. After purification, the DNA was extracted electrophoretically at 10 V into the anodic reservoir (first end port 60) following the electrode configuration of FIG. 5B. For DNA extraction by electrophoresis, both fluid channels and the two elongate central gel channel ports were filled with 1×TBE buffer (Tris-HCl pH 8, boric acid, EDTA). The hydrophobicity of PDMS was exploited to make fluidic contact between first end port 56 and first port 24, and between second end port 58 and second port 26, via pendant droplets of TBE buffer. Platinum electrodes connected to a DC power supply (Keithley 2230G-30-1) were immersed in first end port 56, second end port 58, and first end port 60. First end port 56, second end port 58, first port 24, and second port 26 were grounded, first end port 60 served as the anode and second end port 62 was left floating. Owing to the large pore size of the 0.2 wt. % agarose gel and the indentations created in the gel at cellular locations, rapid electrophoretic extraction of long DNA was achieved without encountering irreversible trapping of DNA within the gel at the 10 V operating electric potential.

Figure 9C:
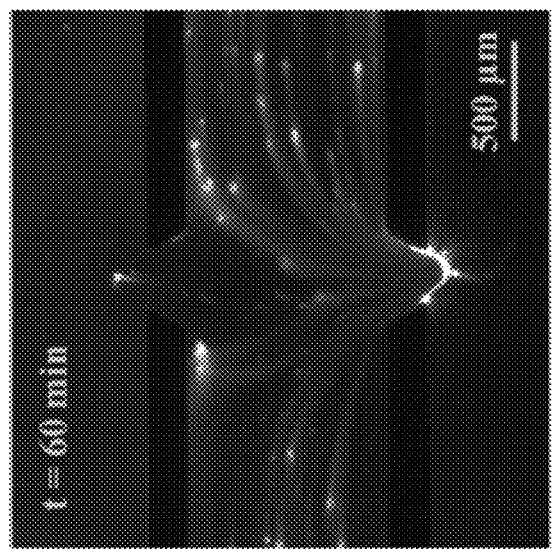
FIGS. 9A-9C are fluorescent images illustrating the effect of electrophoresis time on DNA extraction out of agarose gel.
Figure 9B:
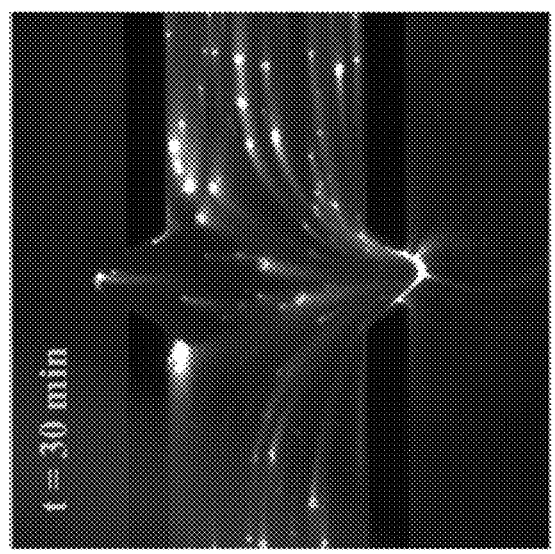
Figure 9A:
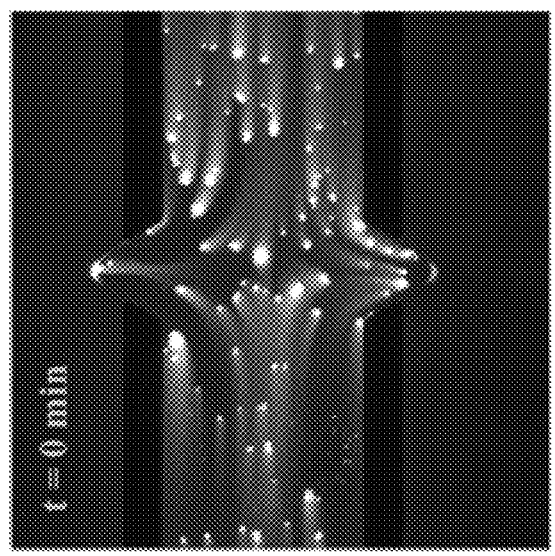

During extraction, some DNA molecules were trapped at the gel-fluid interface and ultimately fragmented during constant voltage electrophoresis. This holdup is currently believed to be due to the entanglements between the DNA and the dangling fibers at the end of the gel. Since the exiting DNA molecule has a higher extension than when in the gel, the transmission of tension along the extended chain to the trapping point causes DNA fragmentation under a constant voltage. To ameliorate this problem, a voltage loop was implemented: 10 V for 18 seconds followed by 0 V for 2 seconds in LabVIEW to assist in periodic chain relaxation for releasing the transient tension along the molecule length. The 2 seconds period for relaxation was determined based on the experimentally observed recoiling time associated with the overhanging chain during electrophoresis. The pulsing is currently believed to allow the released DNA to relax any entanglements with the dangling fibers when compared to the constant voltage case. To expedite the migration of DNA towards first end port 60 after extraction from the gel, the electrode configuration was then changed to have first end port 56, second end port 58, first port 24, and second port 26 floating, first end port 60 as the anode, and second end port 62 as the ground. A potential of 20 V was applied along second side channel 30 of FIG. 1 for 3 minutes after each 7-minute long extraction protocol. The total electrophoresis time of 60 minutes, comprising 6 electrophoresis cycles, was selected based on the fluorescence intensity reduction in the gel, which was recorded by time-lapse imaging of the DNA every 10 minutes using fluorescence microscopy using an sCMOS camera (ANDOR Zyla 4.2), as shown in FIGS. 9A-9C. The small diffusion and electrophoresis time in the miniaturized gel helped to complete the entire DNA extraction from cells in 4 hours, which is significantly faster than both conventional plug lysis (24 hours), as well as commercial platforms performing sample preparation for optical mapping such as the Aurora system (30 hours).

The DNA recovered from the device and any protein contaminants were quantified using fluorometry in a Qubit 2.0 fluorometer (available from Thermo Fisher Scientific), and is shown in Tables 1 and 2.

TABLE 1

| Con- centration (ng/µL) | Run 1 (DNA) | Run 2 (DNA) | DNA | Run 1 (Protein) | Run 2 (Protein) | Protein |
|---|---|---|---|---|---|---|
| Reading 1 | 42 | 57.2 | | 53.1 | 52.9 | |
| Reading 2 | 41.1 | 55.2 | | 52.8 | 52.3 | |
| Reading 3 | 33.9 | 46.9 | | 52.7 | 52.5 | |
| Average | 39 | 53.01 | 46.01 | 52.9 | 52.6 | 52.75 |

TABLE 2

| Concentration (ng/µL) | Device 1 (DNA) | Device 2 (DNA) | Device 3 (Protein) | Device 4 (Protein) | Plug (Protein) |
|---|---|---|---|---|---|
| Reading 1 | 1.87 | 1.81 | 35.9 | 23.7 | 44.3 |
| Reading 2 | 1.85 | 1.88 | 34.9 | 23.5 | 43.7 |
| Reading 3 | 1.84 | 1.89 | 34.7 | 21.6 | 43.1 |
| Average | 1.85 | 1.86 | 35.2 | 22.9 | 43.7 |
| Scaled Average | 0.67 | 0.67 | 11.14 | 7.25 | 13.83 |

15 µL of DNA sample was collected from first end port 60 using a pipette, and mixed with 185 µL of working solution from the dsDNA broad range assay kit. DNA samples from 2 different devices were collected, and 3 measurements were made per sample. To calculate the sample purity based on the DNA:protein ratio, the protein content of the sample was measured in the Qubit 2.0 fluorometer (Table 2). Since the fluorometer reads the fluorescent intensity of molecules bound with specific dyes, the YOYO-labeling of the DNA was accounted for by calibrating with a control solution comprising a mixture of YOYO-labeled λ DNA (16.67 ng µL$^{-1}$) and human histone H4 (16.67 ng µL$^{-1}$) in 1×TBE buffer (Table 1). The control DNA solution was prepared by adding 2.5 µL of stock λ DNA (500 µg mL$^{-1}$, New England Biolabs), YOYO at a concentration of 0.5 µM, and 1.25 µL of stock human histone H4 (1000 µg mL$^{-1}$, BioRad) to 71 µL 1×TBE buffer. The plug prepared DNA at 110 ng µL$^{-1}$ was diluted to 2.2 ng µL$^{-1}$ in 1×TBE buffer, and labeled with YOYO at a concentration of 0.5 µM. The output dsDNA concentration of this control solution in the fluorometer was 46.01 ng µL$^{-1}$, and consequently all DNA readings obtained from the Qubit 2.0 fluorometer were scaled down by a factor of 2.76. The DNA concentrations of the samples recovered from two different devices were 0.671 ng µL$^{-1}$ and 0.674 ng µL$^{-1}$. The volume of DNA sample collected from each device was 15 µL$^{-1}$, giving a yield of 10.05 ng DNA per device. For the starting 12.34 ng DNA seeded in the gel channel in the form of <2000 cells, 81.4% extraction of DNA out of the gel was obtained.

To verify the removal of proteins from the gel, complete digestion of histones was checked for during cell lysis (FIGS. 8A-8D), and the amount of protein in the DNA sample collected from the device was measured using fluorometry. Since the presence of YOYO-labeled DNA can increase the protein signal in the fluorometer due to the broad emission spectra of the dyes, the control solution was used for calibration. The protein concentration of the control solution containing 16.67 ng per µL of histones was measured as 52.75 ng µL$^{-1}$ by the Qubit 2.0 fluorometer, and consequently all protein readings were scaled down by a factor of 3.16. The protein concentration of the samples recovered from two different devices was 11.14 ng µL$^{-1}$ and 7.25 ng µL$^{-1}$. To assess how sample purity compares with DNA prepared from traditional methods, the DNA:protein ratio for samples prepared in the device of this disclosure and for the DNA prepared using conventional plug lysis was compared. The protein reading for the conventional DNA sample diluted to 2.2 ng µL$^{-1}$ was 13.83 ng µL$^{-1}$, giving a DNA:protein ratio of 0.159. The corresponding ratio for the DNA sample prepared in our device was 0.073.

Figure 10:
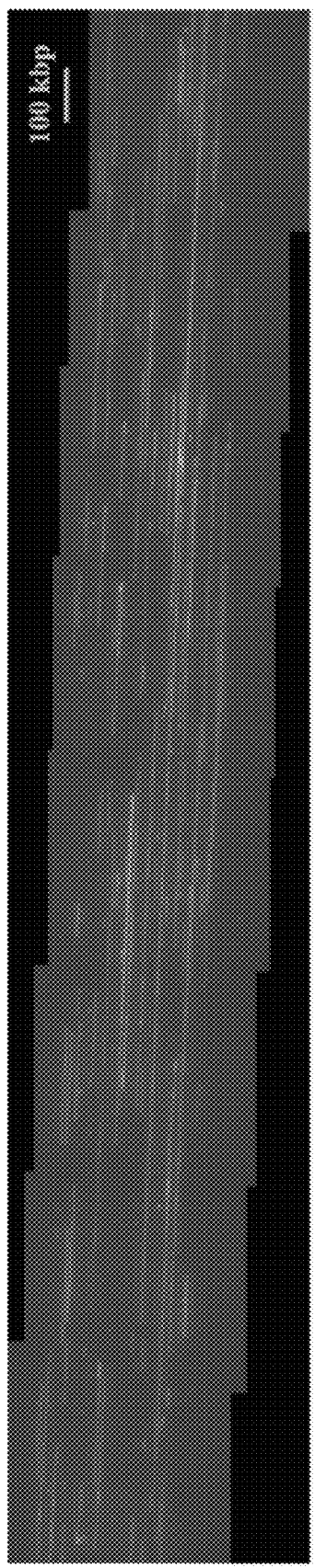
FIG. 10 is a fluorescent image of example YOYO-stained, device-extracted DNA, stretched on silanized glass in a 100 µm wide and 5 µm deep PDMS channel.

The DNA recovered from the DNA extraction device were analyzed by molecular combing in microchannels on activated glass coverslips as shown in FIG. 10. For linearly stretching the DNA, 5 µm deep, 100 µm wide and 10 mm long channels were fabricated in PDMS. After plasma treatment of the PDMS surface, the combing device was bonded to a glass coverslip activated by silanization. Briefly, 22×22 mm² glass coverslips were stacked in a coverslip drying rack and incubated for 7 hours in a 2:1 (v/v) mixture of 70% nitric acid and 37% hydrochloric acid to clean and hydrolyze the glass surface. After washing the coverslips with ultrapure water and drying, they were immersed in a premixed solution of 200 µL N-trimethoxysilylpropyl-N,N, N-trimethylammonium chloride and 53 µL of vinyltrimethoxysilane in 80 mL ultrapure water and incubated for 17 hours at 65° C. The coverslips were washed with water and ethanol, and used immediately for PDMS bonding or stored for up to one week in ethanol at 4° C. 2.5 µL of the DNA solution extracted from the first side port 60 of the device was used to fill 15 channels on a single combing device using capillarity. The stretched single DNA molecules were imaged with an sCMOS camera (ANDOR Zyla 4.2) using a 100× oil objective mounted on an epifluorescence microscope (Leica DMI 4000B). For analyzing the molecules that extended beyond a single image ROI, consecutive images were overlapped using the ImageJ stitching plugin. The use of microchannels for loading DNA during size analysis helps to orient the long molecules in the direction of capillarity, avoiding random overlap of molecules.

Figure 11:
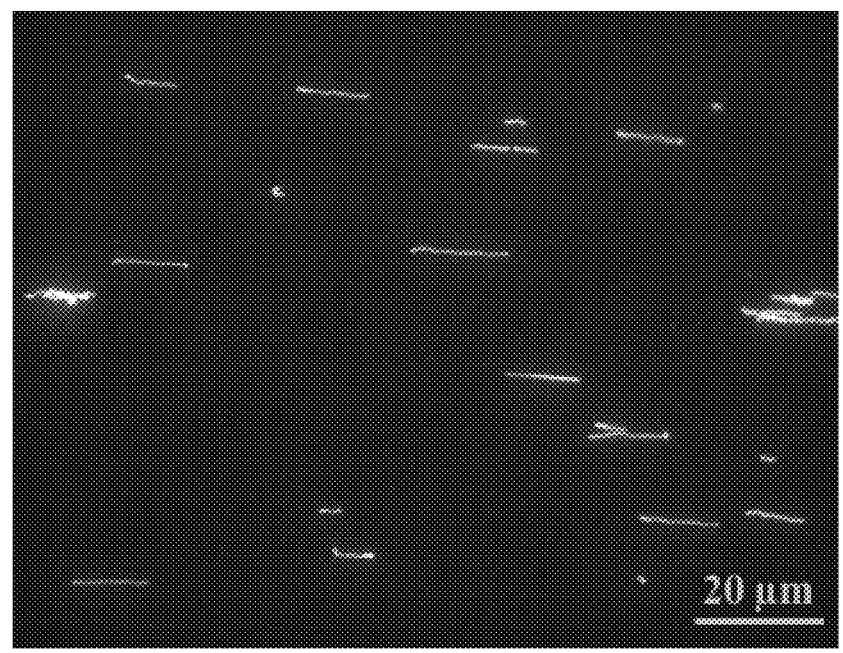
FIG. 11 is an image of example λ DNA stretched on silanized glass in a 100 µm wide and 5 µm deep PDMS channel.
Figure 12:
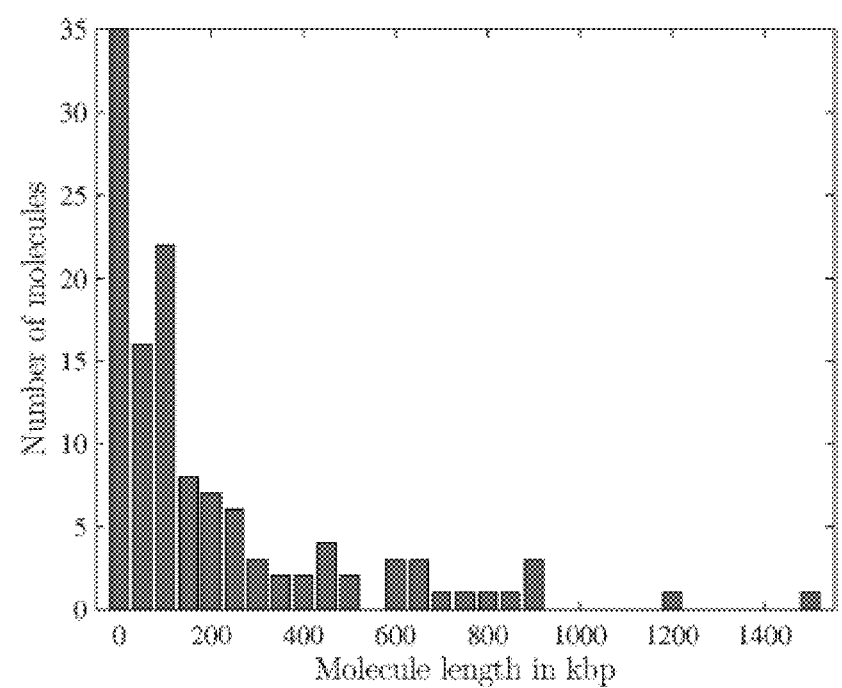
FIG. 12 is a plot of number of DNA molecules versus molecule length in kilobase pairs.
Figure 13:
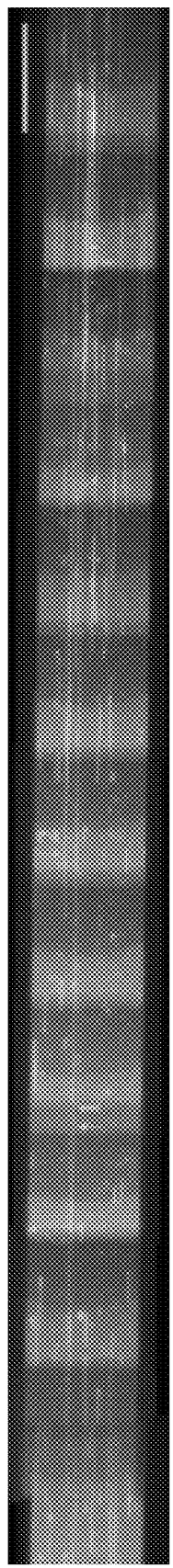
FIG. 13 is an image of example device-extracted DNA stretched on silanized glass in a 100 µm wide and 5 µm deep PDMS channel.

To estimate the size of the molecules based on their pixel length, λ DNA (48.5 kbp) was stretched in the combing device to yield a calibration factor of 3.13 kbp µm$^{-1}$, as shown in FIG. 11. The weight distribution of the representative DNA molecules in FIG. 11 is shown in FIG. 12. The characterized DNA lengths are much in excess of the typical sizes in SMRT sequencing (10-50 kbp) and nanopore sequencing (10-100 kbp). Several molecules in the DNA sample exhibit extensions corresponding to molecular weights of more than 500 kbp, with the longest observed molecule in a separate combing channel being 4 Mbp, as shown in FIG. 13. Molecule 1 is 4070 kbp long and molecule 2 is 2470 kbp long. The scale bar in FIG. 13 represents 300 kbp or 96 µm.

Figure 14:
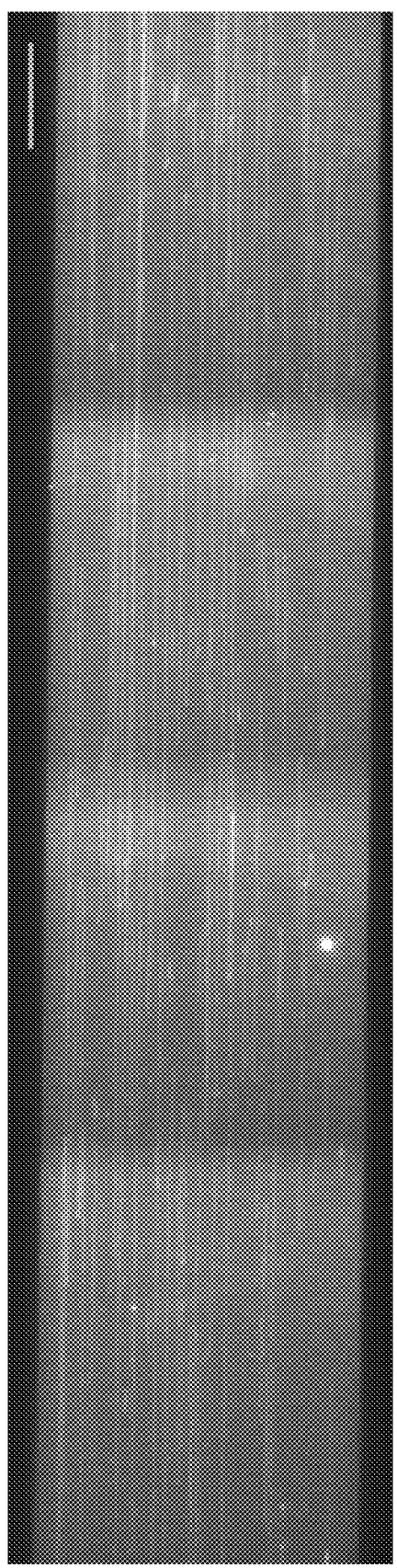
FIG. 14 is an image of example device-extracted DNA stretched on silanized glass in a 100 µm wide and 5 µm deep PDMS channel.

The sample preparation chemistry for certain genomics applications requires working with DNA molecules where the backbone is not fluorescently labeled. To demonstrate the utility of our device for such applications, we performed "blind" sample preparation by not including YOYO in the lysis solution. The DNA were electrophoretically extracted out of the gel and driven to the reservoir 3 using our electrophoresis protocol without visual verification. The recovery of DNA was verified subsequently by adding 2 µL of 0.01 mM YOYO to first end port 60 to stain the DNA, and then stretching these molecules in the combing device. The results are shown in FIG. 14. The scale bar in FIG. 14 represents 100 kbp or 32 µm. Apart from successful blind DNA extraction out of the microgel, this experiment also demonstrates the ability to perform downstream biochemistry on long DNA in the anodic reservoir.

The DNA extraction device described herein utilizes a miniaturized gel to perform long DNA extraction from human cells, reducing the standard day-long protocol to 4 hours. All-liquid-phase DNA extraction from cells is much faster than diffusion-limited DNA extraction in a gel. Unfortunately, liquid phase DNA extraction typically leads to DNA fragmentation due to shearing during processing. Despite all other advantages of the commercially available semi-automated platforms, this particular shortcoming still persists. The DNA extraction device described herein, which uses agarose gel, reduces or substantially eliminates liquid phase shear on the DNA except for the final chip-to-world step, which is necessary at present to interface with genomics technologies.

The DNA purification in the DNA extraction device described herein is accomplished by diffusive molecular exchange, which is enhanced by continuous flow in the fluid channels. The underlying diffusion approach to sample purification is inspired by conventional plug lysis. The cellular debris and digested proteins, being much smaller than genomic DNA, follow the continually replenished concentration gradient to escape out of the gel, and are immediately eliminated out of the device by bulk flow. Due to the use of electrophoresis for DNA purification from cell lysate in commercial sample purification equipment, impurities in the gel in the form of small acidic peptides having low isoelectric points cannot be ruled out completely. After complete gel washing by diffusion, the DNA is extracted in electrophoresis buffer, which theoretically gives pure DNA in buffer while eliminating all possible contaminants like chemical remnants from gel digestion or small negatively charged molecules. On assessment, the DNA:protein ratio of the extracted sample is not dramatically different from that obtained by conventional plug lysis.

Post-processing of the extracted long DNA such as nick-labeling for genome mapping and adapter ligation for nanopore sequencing involve complex and sequential chemistry steps. In conventional protocols, typically there is no elimination of past reagents from the genomic sample, which can interfere with the genomic analysis. Microfluidic platforms demonstrating enzymatic labeling, concentration and purification of DNA have been reported; however they take DNA as input, and to date have been shown to work with relatively small λ DNA (48.5 kilobase pairs). The temperature-sensitive chemical lysis of cells, YOYO labeling of the released genomic DNA, and cellular waste elimination from the DNA extraction device described herein constitute a proof-of-concept demonstration of not only the ability to execute chemistry on cells as well as DNA in the gel, but also the efficient elimination of unwanted reagents after their role in sample processing is complete. The extracted DNA product can then be directly loaded into genomics chips.

The DNA extraction device described herein has a simple design and employs reusable external electrodes for DNA extraction by electrophoresis. The incorporation of on-chip electrophoresis in the method described herein demonstrates the tunability of the devices to drive the extracted DNA around without manually probing it. World-to-chip interfacing to transfer long DNA samples to genomics chips without molecule fragmentation and sample loss is a serious and yet unaddressed problem in long-read sequencing. In current tube-based protocols, use of a pipette for transfer is inevitable. Being a microfluidic approach, the DNA extraction device described herein has the potential to be integrated with genomics chips, serving as a powerful tool to deliver ultra-long DNA directly from cells to genomic analysis technologies without any human intervention. Although single-cell DNA isolation for either linearization in nanochannels or optical mapping in nanoslits have been demonstrated on a single device, there is yet no generic sample preparation platform that can be used upstream of any genomic analysis technology.

The DNA extracted from the DNA extraction device described herein are hundreds of kilobases long, in line with the requirement of current long-read genomics technologies. Many long DNA preparation techniques extract native DNA out of cells, but the fragment size is successively reduced throughout the process. In this work, DNA molecules as long as 4 Mbp were recovered out of the device and demonstrated their integrity in a secondary environment. At present, it is challenging to establish the overall molecular weight distribution produced by the device. Due to the typical molecular weights observed, sample sizing techniques are limited to pulsed-field gel electrophoresis or molecule extension either by nanochannel confinement or molecular combing. While pulsed-field requires very high concentration input DNA, nanochannel confinement requires sophisticated nanofluidics chips. Molecular combing in microchannels is relatively straightforward for visualization and elementary DNA sizing if performed at a low DNA concentration to avoid molecular overlap, but it requires high throughput machine-vision to analyze hundreds of fields of view across many combing channels and obtain a statistically significant molecular weight distribution. The manually obtained distribution in FIG. 12 is for the 122 molecules in the 8 fields of view stitched in FIG. 10, which, although illustrative of the presence of long DNA, represents a very small fraction of the total DNA recovered and combed from the device. Long-read genomics technologies such as nanopore sequencing and genome mapping in nanochannels capture the DNA fragment size during each run to report their observed read lengths, and it is anticipated that these end-applications will ultimately prove to be a more accurate validation of the sample preparation approach described herein.

The presented approach produces tens of nanograms of DNA from a few thousand cells as input, in line with the emerging inclination towards using genomics technologies for personalizing treatment via analysis of patient samples. While it is possible to sequence small amounts of DNA in long-read technologies, typical protocols currently employ amplification of the low abundance input sample, which will be challenging to implement accurately for very long molecules. The most straightforward approach to overcome this challenge is to pool samples from multiple devices. Additionally, extensive device multiplexing can be implemented and all the DNA can be eluted in a common outlet to produce high concentration samples. To increase the DNA yield from a single device, the gel-fluid overlap region, demarcated by the trapezoidal channels, can be elongated by patterning multiple parallel trapezoidal posts similar to cell culture devices. For such geometries, the potential drop across the gel can be increased by fabricating deeper fluid channels while leaving the gel channel depth, and hence the Laplace pressure, unaltered. Alternatively, in the case of a longer gel overlap, electrodes can either be injected into another side channel, or be patterned on the glass slide such that, after PDMS bonding, they align parallel to the gel channel on either side to ensure a strong electric field in the overlapping gel region. The DNA can then be directed to either reservoir by using external reservoir electrodes.

Various examples have been described. These and other examples are within the scope of the following claims.

What is claimed is:

1. A DNA extraction device comprising:
a substrate defining:
an elongate central channel defining a major axis, wherein a width of the elongate central channel measured perpendicular to the major axis and in a major plane of the substrate is greater than a depth of the elongate central channel measured perpendicular to the major axis and perpendicular to the major plane of the substrate, and wherein the depth of the elongate central channel is less than about 15 times a diameter of a cell to be introduced in the elongate central channel;
a first side channel adjacent to the elongate central channel on a first side of the major axis;
a second side channel adjacent to the elongate central channel on a second side of the major axis, wherein the second side is opposite the first side;
a single first trapezoidally shaped connecting channel connecting the first side channel and the elongate central channel, wherein a smaller parallel side of the single first trapezoidally shaped connecting channel is open to the first side channel, and wherein the single first trapezoidally shaped connecting channel is the only channel connecting the first side channel and the elongate central channel;
a single second trapezoidally shaped connecting channel connecting the second side channel and the elongate central channel, wherein a smaller parallel side of the single second trapezoidally shaped connecting channel is open to the second side channel, and wherein the single second trapezoidally shaped connecting channel is the only channel connecting the second side channel and the elongate central channel;
at least one first side channel electrode;
at least one second side channel electrode; and
a voltage source connected between the at least one first side channel electrode and the at least one second side channel electrode, wherein the first side channel, the second side channel, the single first trapezoidally shaped connecting channel, and the single second trapezoidally shaped connecting channel shape an electric field generated by the voltage source to focus a voltage drop across the first and second trapezoidally shaped connecting channels.

2. The DNA extraction device of claim 1, further comprising at least one elongate central channel electrode.

3. The DNA extraction device of claim 1, wherein a width of the smaller parallel side of the single first trapezoidally shaped connecting channel and a width of the smaller parallel side of the single second trapezoidally shaped connecting channel are greater than the depth of the elongate central channel.

4. The DNA extraction device of claim 1, wherein an internal angle of the single first trapezoidally shaped connecting channel is about 60°.

5. The DNA extraction device of claim 1, wherein the depth of the elongate central channel is greater than the diameter of the cell to be introduced in the elongate central channel.

6. The DNA extraction device of claim 1, wherein the depth of the elongate central channel is less than about ten times the diameter of the cell to be introduced in the elongate central channel.

7. The DNA extraction device of claim 1, wherein the first side channel comprises a central portion defining a first side channel major axis extending generally parallel to the major axis of the elongate central channel, a first end portion extending from a first end of the central portion and diverging from the major axis of the elongate central channel, and a second end portion extending from a second end of the central portion and diverging from the major axis of the elongate central channel.

8. The DNA extraction device of claim 7, wherein the second side channel comprises a central portion defining a second side channel major axis extending generally parallel to the major axis of the elongate central channel, a first end portion extending from a first end of the central portion and diverging from the major axis of the elongate central channel, and a second end portion extending from a second end of the central portion and diverging from the major axis of the elongate central channel.

9. The DNA extraction device of claim 8, wherein the at least one first side channel electrode comprises two first side channel electrodes, one first side channel electrode positioned at an end of the first end portion of the first side channel and another first side channel electrode positioned at an end of the second end portion of the first side channel, and wherein the at least one second side channel electrode comprises two second side channel electrodes, one second side channel electrode positioned at an end of the first end portion of the second side channel and another second side channel electrode positioned at an end of the second end portion of the second side channel.

10. The DNA extraction device of claim 1, wherein the voltage source comprises a DC voltage source.

11. The DNA extraction device of claim 1, wherein the voltage source comprises an AC voltage source.

12. The DNA extraction device of claim 1, further comprising a gel and a cell sample disposed in the elongate central channel.

13. A method comprising:
introducing a gel and a cell sample in an elongate central channel of a DNA extraction device, wherein the DNA extraction device comprises: the elongate central channel defining a major axis, wherein a width of the elongate central channel measured perpendicular to the major axis and in a major plane of a substrate is greater than a depth of the elongate central channel measured perpendicular to the major axis and perpendicular to the major plane of the substrate, and wherein the depth of the elongate central channel is less than about 15 times a diameter of a cell to be introduced in the elongate central channel;
a first side channel adjacent to the elongate central channel on a first side of the major axis;
a second side channel adjacent to the elongate central channel on a second side of the major axis, wherein the second side is opposite the first side;
a single first trapezoidally shaped connecting channel connecting the first side channel and the elongate central channel, wherein a smaller parallel side of the single first trapezoidally shaped connecting channel is open to the first side channel, and wherein the single first trapezoidally shaped connecting channel is the only channel connecting the first side channel and the elongate central channel;
a single second trapezoidally shaped connecting channel connecting the second side channel and the elongate central channel, wherein a smaller parallel side of the single second trapezoidally shaped connecting channel is open to the second side channel, and wherein the single second trapezoidally shaped connecting channel is the only channel connecting the second side channel and the elongate central channel;
introducing a cell lysis solution to at least one of the first side channel or the second side channel to cause the cell lysis solution to enter into the elongate central channel and lyse cells in the cell sample;
introducing an electrophoresis buffer solution to at least one of the first side channel or the second side channel to cause the electrophoresis buffer solution to enter into the elongate central channel;
placing at least one first side channel electrode in the first side channel and at least one second side channel electrode in the second side channel; and
applying a voltage between the at least one first side channel electrode and the at least one second side channel electrode to accumulate DNA from the cell sample into at least one of the first side channel or the second side channel, wherein the first side channel, the second side channel, the single first trapezoidally shaped connecting channel, and the single second trapezoidally shaped connecting channel shape an electric field generated by a voltage source to focus a voltage drop across the first and second trapezoidally shaped connecting channels.

14. The method of claim 13, further comprising placing at least one elongate central channel electrode in the elongate central channel, and wherein applying the voltage comprises applying a voltage between the at least one first side channel electrode, the at least one second side channel electrode, and the at least one elongate central channel electrode.

15. The method of claim 1, further comprising, after introducing the cell lysis solution and before introducing the electrophoresis buffer solution, introducing a wash solution to at least one of the first side channel or the second side channel to cause the wash solution to enter into the elongate central channel to remove lysed cellular material.

16. The method of claim 13, wherein a width of the smaller parallel side of the single first trapezoidally shaped connecting channel and a width of the smaller parallel side of the single second trapezoidally shaped connecting channel are greater than the depth of the elongate central channel.

17. The method of claim 13, wherein an internal angle of the single first trapezoidally shaped connecting channel is about 60°.

18. The method of claim 13, wherein the depth of the elongate central channel is greater than the diameter of the cell to be introduced in the elongate central channel.

19. The method of claim 13, wherein the first side channel comprises a central portion defining a first side channel major axis extending generally parallel to the major axis of the elongate central channel, a first end portion extending from a first end of the central portion and diverging from the major axis of the elongate central channel, and a second end portion extending from a second end of the central portion and diverging from the major axis of the elongate central channel.

20. The method of claim 19, wherein the second side channel comprises a central portion defining a second side channel major axis extending generally parallel to the major axis of the elongate central channel, a first end portion extending from a first end of the central portion and diverging from the major axis of the elongate central channel, and a second end portion extending from a second end of the central portion and diverging from the major axis of the elongate central channel.

21. The method of claim 13, wherein applying the voltage between the at least one first side channel electrode and the at least one second side channel electrode comprises applying a pulsed DC voltage between the at least one first side channel electrode and the at least one second side channel electrode.

* * * * *